US012702369B2

(12) United States Patent
Rao et al.

(10) Patent No.: US 12,702,369 B2
(45) Date of Patent: Aug. 11, 2026

(54) ACTIVE PIXEL SENSORS FOR PHOTON COUNTING X-RAY DETECTORS

(71) Applicant: GE Precision Healthcare LLC, Wauwatosa, WI (US)

(72) Inventors: Naresh Kesavan Rao, Clifton Park, NY (US); Biju Jacob, Niskayuna, NY (US); Collin William Hitchcock, Clifton Park, NY (US)

(73) Assignee: GE Precision Healthcare LLC, Waukesha, WI (US)

( * ) Notice: Subject to any disclaimer, the term of this patent is extended or adjusted under 35 U.S.C. 154(b) by 550 days.

(21) Appl. No.: 18/133,051

(22) Filed: Apr. 11, 2023

(65) Prior Publication Data

US 2024/0341704 A1 Oct. 17, 2024

(51) Int. Cl.

*A61B 6/42* (2024.01)
*A61B 6/03* (2006.01)
*G01T 1/24* (2006.01)

(52) U.S. Cl.

CPC ............ *A61B 6/4241* (2013.01); *G01T 1/247* (2013.01); *A61B 6/03* (2013.01)

(58) Field of Classification Search

CPC .......... A61B 6/03; A61B 6/4241; G01T 1/247
See application file for complete search history.

(56) References Cited

U.S. PATENT DOCUMENTS 4,803,710 A * 2/1989 Elabd ..................... G11C 27/04 257/241
5,943,388 A * 8/1999 Tumer .................. G01V 5/226 378/98.9
6,243,441 B1 * 6/2001 Zur ......................... G01T 1/247 378/98.7
9,588,240 B1 * 3/2017 Kouada .................. H04N 25/30
11,041,968 B2 6/2021 Danielsson et al.
11,054,371 B2 7/2021 Danielsson
(Continued)

FOREIGN PATENT DOCUMENTS

WO 2022233699 A1 11/2022

OTHER PUBLICATIONS

EP application 24164495.4 filed Mar. 19, 2024—extended Search Report issued Sep. 9, 2024, 8 pages.
(Continued)

*Primary Examiner* — Blake C Riddick
(74) *Attorney, Agent, or Firm* — Fletcher Yoder, P.C.

(57) ABSTRACT

A photon counting detector includes a plurality of detector sub-modules. Each detector sub-module includes a semiconductor substrate. Each detector sub-module also includes a plurality of active pixels configured to act as detector elements disposed on the semiconductor substrate. Each detector sub-module further includes a plurality of traces extending from the plurality of active pixels to readout circuitry. Each active pixel of the plurality of active pixels is coupled to a respective trace of the plurality of traces. Each active pixel includes an amplification stage configured to generate an output signal based on a current pulse output generated by the active pixel. The photon counting detector also includes the readout circuitry configured to directly read out the output signals from the plurality of active pixels, wherein the readout circuitry is separate from the plurality of detector sub-modules.

18 Claims, 15 Drawing Sheets

(56) References Cited

U.S. PATENT DOCUMENTS

| | | | | |
|---|---|---|---|---|
| 11,150,361 | B2 | 10/2021 | Danielsson et al. | |
| 2004/0017224 | A1* | 1/2004 | Tumer | H04N 25/773 327/51 |
| 2005/0139757 | A1* | 6/2005 | Iwanczyk | G01T 1/2928 257/E31.015 |
| 2007/0003006 | A1* | 1/2007 | Tkaczyk | G01T 1/242 378/19 |
| 2008/0210878 | A1* | 9/2008 | Friedman | G01J 1/42 250/374 |
| 2009/0224167 | A1* | 9/2009 | Blevis | G01T 1/241 250/370.08 |
| 2009/0251125 | A1* | 10/2009 | Hawver | G01T 1/247 323/355 |
| 2010/0148082 | A1* | 6/2010 | Du | G01T 1/00 250/370.13 |
| 2010/0320391 | A1* | 12/2010 | Antonuk | H10F 39/026 257/E31.124 |
| 2011/0210235 | A1* | 9/2011 | Dierickx | G01T 1/17 250/214 R |
| 2012/0228486 | A1* | 9/2012 | Herrmann | G01T 1/243 250/252.1 |
| 2013/0044248 | A1* | 2/2013 | Tumer | H03F 3/45475 348/E5.091 |
| 2013/0161523 | A1* | 6/2013 | Tkaczyk | G01T 1/241 257/E31.124 |
| 2014/0183607 | A1* | 7/2014 | Liu | H10F 39/189 257/292 |
| 2015/0312501 | A1* | 10/2015 | Fahim | H04N 25/707 348/294 |
| 2016/0084968 | A1* | 3/2016 | Blevis | G01T 1/24 250/371 |
| 2016/0381311 | A1* | 12/2016 | Guo | H04N 25/46 348/308 |
| 2017/0230597 | A1* | 8/2017 | Fahim | H04N 25/30 |
| 2019/0383955 | A1 | 12/2019 | Hjärn et al. | |
| 2020/0158663 | A1* | 5/2020 | Danielsson | G01T 1/247 |
| 2020/0158895 | A1* | 5/2020 | Danielsson | A61B 6/032 |
| 2020/0158896 | A1* | 5/2020 | Danielsson | G01T 1/243 |
| 2021/0186440 | A1 | 6/2021 | Kreisler | |
| 2021/0349223 | A1* | 11/2021 | Harris | G01T 1/247 |
| 2022/0357468 | A1* | 11/2022 | Junnarkar | G01T 1/175 |
| 2024/0159924 | A1* | 5/2024 | Iniewski | H10F 39/1895 |

OTHER PUBLICATIONS

Förster et al., "Transforming X-ray detection with hybrid photon counting detectors," The Royal Society Publishing, 2019, 15 pgs.

Cheng et al., "Study of current-mode active pixel sensor circuits using amorphous InSnZNO thin-film transistor for 50-Im pixel-pitch indirect X-ray imagers," Elsevier Ltd., 2017, pp. 53-64.

Karim et al., "Amorphous Silicon Active Pixel Sensor Readout Circuit for Digital Imaging," IEEE Transactions on Electron Devices, Jan. 2003, vol. 50, No. 1, 10 pgs.

* cited by examiner

ACTIVE PIXEL SENSORS FOR PHOTON COUNTING X-RAY DETECTORS

BACKGROUND

The subject matter disclosed herein relates to X-ray detectors and, more particularly, to active pixel sensors for photon counting X-ray detectors.

Non-invasive imaging technologies allow images of the internal structures or features of a subject (patient, manufactured good, baggage, package, or passenger) to be obtained without physical contact.

For example, in X-ray-based imaging technologies, X-ray radiation penetrates a subject of interest, such as a human patient, and a portion of the radiation impacts a detector where the intensity data is collected. In digital X-ray systems, a detector produces signals representative of the amount or intensity of radiation impacting discrete pixel regions of a detector surface. The signals may then be processed to generate an image that may be displayed for review.

In one such X-ray based technique, known as computed tomography (CT), a scanner may project fan-shaped or cone-shaped X-ray beams from an X-ray source at numerous view angle positions about an object being imaged, such as a patient. The X-ray beams are attenuated as they traverse the object and are detected by a set of detector elements which produce signals representing the intensity or number of incident X-rays reaching the detector. The signals are processed to produce data representing the line integrals of the linear attenuation coefficients of the object along the X-ray paths. These signals are typically called "projection data" or just "projections". By using reconstruction techniques, such as filtered backprojection, images may be generated that represent a cross sectional slice or three-dimensional (3D) volume of a region of interest of the patient or imaged object. In a medical context, pathologies or other structures of interest may then be located or identified from the reconstructed images or rendered volume.

Some CT detectors include photon counting detectors. A photon counting detector converts each detected X-ray photon in the energy unit (keV) into a voltage pulse in the pulse height unit (mV). An X-ray photon is absorbed in a semiconductor material (e.g., cadmium zinc telluride (CZT), silicon, etc.) resulting in generation of photocharge proportional to the X-ray photon energy. A photodiode or diode, separates the electron-hole pairs and generates a current pulse at its output. The current is fed into application-specific integrated circuit (ASIC), which tracks individual current pulses, determines the energy of the X-ray photons that generated these pulses and assigns them to the appropriate energy bins.

In the state-of-the-art photon counting detectors, the semiconductor sensor, consisting of an array of photodiode pixels, is a separate layer to which the ASICs are attached by direct wire-bonding. This heterogeneous integration puts a large capacitance load to the input charge sensitive amplifier (CSA) of the ASIC and increases the noise and power consumption of the system.

BRIEF DESCRIPTION

A summary of certain embodiments disclosed herein is set forth below. It should be understood that these aspects are presented merely to provide the reader with a brief summary of these certain embodiments and that these aspects are not intended to limit the scope of this disclosure. Indeed, this disclosure may encompass a variety of aspects that may not be set forth below.

In an embodiment, a photon counting detector is provided. The photon counting detector includes a plurality of detector sub-modules. Each detector sub-module includes a semiconductor substrate. Each detector sub-module also includes a plurality of active pixels configured to act as detector elements disposed on the semiconductor substrate. Each detector sub-module further includes a plurality of traces extending from the plurality of active pixels to readout circuitry. Each active pixel of the plurality of active pixels is coupled to a respective trace of the plurality of traces. Each active pixel includes an amplification stage configured to generate an output signal based on a current pulse output generated by the active pixel. The photon counting detector also includes the readout circuitry configured to directly read out the output signals from the plurality of active pixels, wherein the readout circuitry is separate from the plurality of detector sub-modules.

In another embodiment, a computed tomography (CT) imaging system is provided. The CT imaging system includes a photon counting detector. The photon counting detector includes at least one detector sub-module. The at least one detector sub-module includes a semiconductor substrate. The at least one detector sub-module also includes a plurality of active pixels configured to act as detector elements disposed on the semiconductor substrate. The at least one detector sub-module further includes a plurality of traces extending from the plurality of active pixels to readout circuitry. Each active pixel of the plurality of active pixels is coupled to a respective trace of the plurality of traces. Each active pixel includes an amplification stage configured to generate an output signal based on a current pulse output generated by the active pixel. The photon counting detector also includes the readout circuitry configured to directly read out the output signals from the plurality of active pixels, wherein the readout circuitry is separate from the at least one detector sub-module.

In a further embodiment, a photon counting detector is provided. The photon counting detector includes at least one detector sub-module. The at least one detector sub-module includes a semiconductor substrate. The at least one detector sub-module also includes a plurality of active pixels configured to act as detector elements disposed on the semiconductor substrate. The at least one detector sub-module includes a plurality of traces extending from the plurality of active pixels to readout circuitry. Each active pixel of the plurality of active pixels is coupled to a respective trace of the plurality of traces. Each active pixel is configured to act as a passive integrator, and wherein each active pixel comprises a transconductance amplifier comprising a single transistor configured to generate an output signal based on a current pulse output generated by the active pixel. The photon counting detector also includes the readout circuitry configured to directly read out the output signals from the plurality of active pixels, wherein the readout circuitry is separate from the at least one detector sub-module, and wherein the readout circuitry comprises a current source biased to the single transistor.

In an even further embodiment, a photon counting detector is provided. The photon counting detector includes a plurality of detector sub-modules. Each detector sub-module includes a semiconductor layer. Each detector sub-module also includes a plurality of active pixels configured to act as detector elements disposed on the semiconductor substrate. Each detector sub-module further includes a plurality of traces extending from the plurality of active pixels to readout circuitry. Each active pixel of the plurality of active pixels is coupled to a respective trace of the plurality of traces. Each active pixel includes a bipolar junction transistor configured to generate an output signal, wherein the output signal is an amplified signal of a current pulse generated by the active pixel in response to an X-ray photon impacting the semiconductor substrate. The photon counting detector also includes the readout circuitry configured to directly read out the output signals from the plurality of active pixels, wherein the readout circuitry is separate from the plurality of detector sub-modules.

BRIEF DESCRIPTION OF THE DRAWINGS

These and other features, aspects, and advantages of the present subject matter will become better understood when the following detailed description is read with reference to the accompanying drawings in which like characters represent like parts throughout the drawings, wherein.

DETAILED DESCRIPTION

Figure 1:
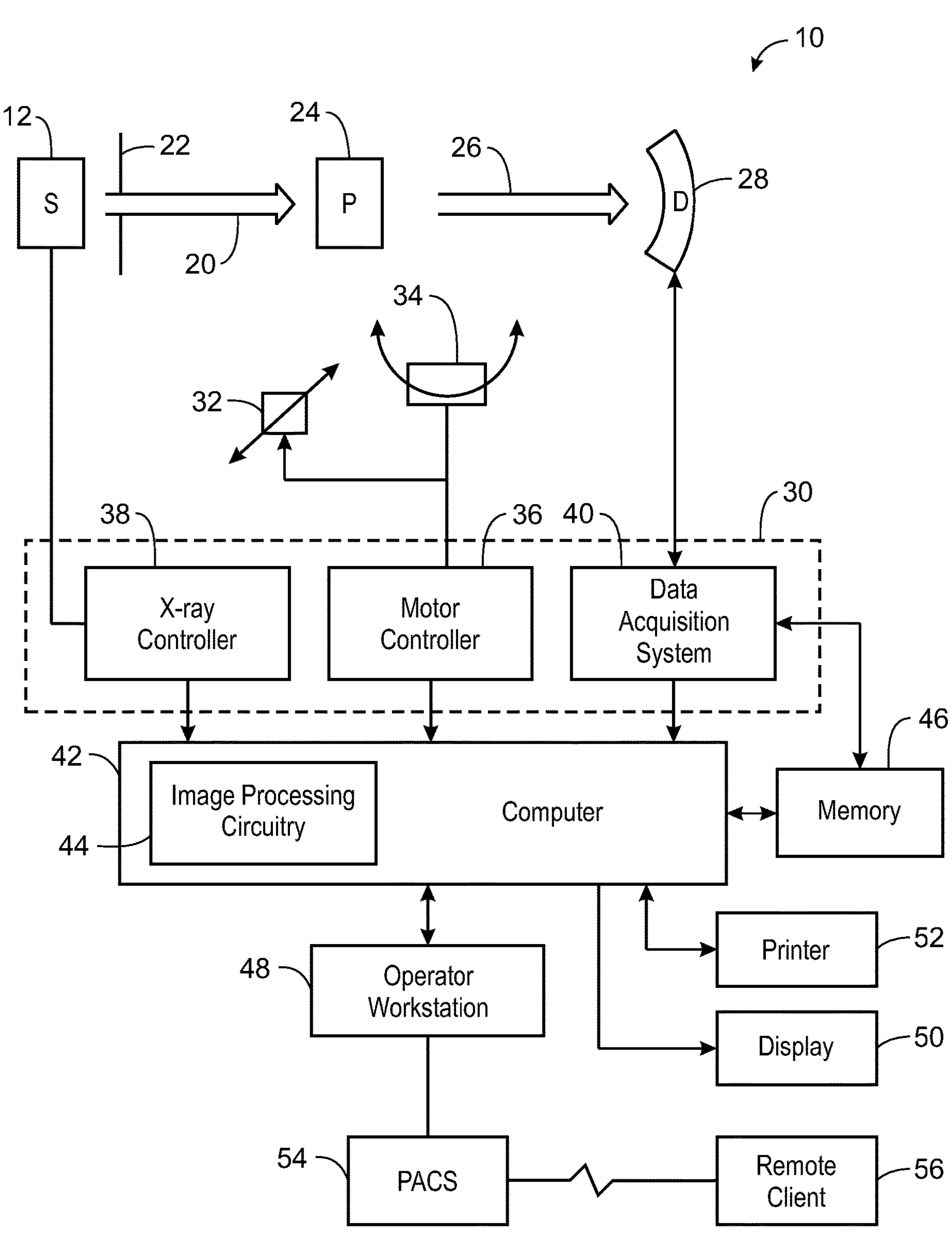
FIG. 1 is a block diagram representation of a CT system, in accordance with aspects of the present disclosure.

One or more specific embodiments will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present subject matter, the articles "a," "an," "the," and "said" are intended to mean that there are one or more of the elements. The terms "comprising," "including," and "having" are intended to be inclusive and mean that there may be additional elements other than the listed elements. Furthermore, any numerical examples in the following discussion are intended to be non-limiting, and thus additional numerical values, ranges, and percentages are within the scope of the disclosed embodiments.

While the following discussion is generally provided in the context of medical imaging, it should be appreciated that the present techniques are not limited to such medical contexts. Indeed, the provision of examples and explanations in such a medical context is only to facilitate explanation by providing instances of real-world implementations and applications. However, the present approaches may also be utilized in other contexts, such as the non-destructive inspection of manufactured parts or goods (i.e., quality control or quality review applications), and/or the non-invasive inspection of packages, boxes, luggage, and so forth (i.e., security or screening applications). In general, the present approaches may be desirable in any imaging or screening context in which a photon counting detector is utilized.

Energy-resolved, photon counting detectors can provide spectral information that is not available with conventional energy-integrating detectors. One type of energy-discriminating, photon counting detection technology employs silicon strips as a direct-conversion sensor material. Use of silicon as the direct-conversion material may provide a higher count rate capability than may be obtained with other direct-conversion materials, such as CZT or CdTe. In certain embodiments, the detector may be arranged edge-on to increase absorption efficiency by enabling an absorption depth to be chosen to any length and the detector can still be fully depleted without going to very high voltages. The detector elements on detector sub-modules or sensors (in particular those detector elements along an edge of the detector sub-module or sensor) are typically coupled to ASICS (which are separate from the detector sub-modules) via direct wire-bonding. This heterogenous integration puts a large capacitance load to the input CSA of the ASIC and increases the noise and power consumption of the system.

The present approaches mitigate this problem by implementing a practical active pixel sensor for the photon counting system (photon counting detector). In particular, each detector sub-module includes one or more active pixels (e.g., diodes and associated circuitry) includes an amplification stage to overcome the noise impact of the detector capacitance. The amplification stage is integrated with the pixel to provide current gain to increase signal-to-noise ratio to suppress the noise impact of the detector capacitance. The output signal from the amplification stage is directly readout by the readout circuitry (e.g., ASIC) which is separate from the detector sub-modules. In certain embodiments, each active pixel is configured to act as a passive integrator. In this embodiment, the amplification stage includes a transconductance amplifier having a single transistor. In this embodiment, the current source is located in the readout circuitry and is biased to the single transistor. In certain embodiments, the amplification stage includes a charge sensitive amplifier. In this embodiment, the amplification stage includes a first transistor and a second transistor, where the first transistor is the charge sensitive amplifier and the second transistor is configured to convert a voltage output to current. In this embodiment, a current source is integrated in each active pixel and the active pixel lacks a bias circuit. These techniques improve the performance of silicon-based photon counting detectors, such as computed tomography detectors or other suitable types of radiographic X-ray detectors. In particular, the disclosed techniques directly improve image quality due to lowering the effects of electronic noise (due to improved signal-to-noise ratio). In addition, the disclosed techniques reduce both system complexity and cost due to lower readout circuitry (e.g., ASIC) power consumption.

With the preceding discussion in mind, FIG. 1 illustrates an embodiment of an imaging system 10 for acquiring and processing image data utilizing the active pixels discussed herein. Although the following embodiments are discussed in terms of the computed tomography (CT) imaging system, the embodiments may also be utilized with other imaging systems (e.g., X-ray, PET, CT/PET, SPECT, nuclear CT, etc.). In the illustrated embodiment, system 10 is a computed tomography (CT) system designed to acquire X-ray projection data, to reconstruct the projection data into a tomographic image, and to process the image data for display and analysis. The CT imaging system 10 includes one or more X-ray sources 12, such as one or more X-ray tubes or solid-state emission structures which allow X-ray generation at one or more locations and/or one or more energy spectra during an imaging session.

In certain implementations, the source 12 may be positioned proximate to a collimator 22 used to define the size and shape of the one or more X-ray beams 20 that pass into a region in which a subject 24 (e.g., a patient) or object of interest is positioned. The subject 24 attenuates at least a portion of the X-rays. Resulting attenuated X-rays 26 impact a detector array 28 formed by a plurality of detector elements (e.g., pixels). As discussed herein, the detector 28 may be a photon counting detector, including an energy-discriminating photon counting detector, whose outputs convey information about the number and energy of photons that impact the detector at measured positions and over a time interval corresponding to a scan or imaging session. In certain such embodiments, the energy-discriminating, photon counting detector may be a direct-conversion type detector (i.e., not employing a scintillator intermediary), such as a detector based on silicon strips. In certain embodiments, the detector array 28 may be formed by a plurality of detector sub-modules or sensors (each having a plurality of detector elements such as photodiode or diodes). In certain embodiments, the detector array 28 and the detector sub-modules may be an edge-on detector and edge-on detector sub-modules configured for edge illumination from the X-rays (i.e., the X-rays enter through the edge of the detector sub-modules). In particular, the detector array 28 may be structured similar to the detectors disclosed in U.S. Publication No. 2019/0383955 filed Feb. 19, 2019 and titled "X-ray Detector System Design", which is incorporated herein in its entirety for all purposes.

Each detector element produces an electrical signal that represents the intensity of the incident X-ray photons (e.g., the energy and number of incident photons) at the position of the detector element when the beam strikes the detector 28. Electrical signals are acquired and processed to generate one or more scan datasets.

A system controller 30 commands operation of the imaging system 10 to execute examination and/or calibration protocols and to process the acquired data. With respect to the X-ray source 12, the system controller 30 furnishes power, focal spot location, control signals and so forth, for the X-ray examination sequences. The detector 28 is coupled to the system controller 30, which commands acquisition of the signals generated by the detector 28. In addition, the system controller 30, via a motor controller 36, may control operation of a linear positioning subsystem 32 and/or a rotational subsystem 34 used to move components of the imaging system 10 and/or the subject 24. The system controller 30 may include signal processing circuitry and associated memory circuitry. In such embodiments, the memory circuitry may store programs, routines, and/or encoded algorithms executed by the system controller 30 to operate the imaging system 10, including the X-ray source 12, and to process the data acquired by the detector 28 in accordance with the steps and processes discussed herein. In one embodiment, the system controller 30 may be implemented as all or part of a processor-based system such as a general purpose or application-specific computer system.

The source 12 may be controlled by an X-ray controller 38 contained within the system controller 30. The X-ray controller 38 may be configured to provide power and timing signals to the source 12. In addition, in some embodiments the X-ray controller 38 may be configured to selectively activate the source 12 such that tubes or emitters at different locations within the system 10 may be operated in synchrony with one another or independent of one another.

The system controller 30 may include a data acquisition system (DAS) 40. The DAS 40 receives data collected by readout electronics (e.g., ASICs) of the detector 28, such as sampled analog signals from the detector 28. The DAS 40 may then convert the data to digital signals for subsequent processing by a processor-based system, such as a computer 42. In other embodiments, the detector 28 may convert the sampled analog signals to digital signals prior to transmission to the data acquisition system 40. The computer may include processing circuitry 44 (e.g., image processing circuitry). The computer 42 may include or communicate with one or more non-transitory memory devices 46 that can store data processed by the computer 42, data to be processed by the computer 42, or instructions to be executed by a processor (e.g., processing circuitry 44) of the computer 42. For example, the processing circuitry 44 of the computer 42 may execute one or more sets of instructions stored on the memory 46, which may be a memory of the computer 42, a memory of the processor, firmware, or a similar instantiation.

The computer 42 may also be adapted to control features enabled by the system controller 30 (i.e., scanning operations and data acquisition), such as in response to commands and scanning parameters provided by an operator via an operator workstation 48. The system 10 may also include a display 50 coupled to the operator workstation 48 that allows the operator to view relevant system data, imaging parameters, raw imaging data, reconstructed data, and so forth. Additionally, the system 10 may include a printer 52 coupled to the operator workstation 48 and configured to print any desired measurement results. The display 50 and the printer 52 may also be connected to the computer 42 directly or via the operator workstation 48. Further, the operator workstation 48 may include or be coupled to a picture archiving and communications system (PACS) 54. PACS 54 may be coupled to a remote system 56, radiology department information system (RIS), hospital information system (HIS) or to an internal or external network, so that others at different locations can gain access to the image data.

Figure 2:
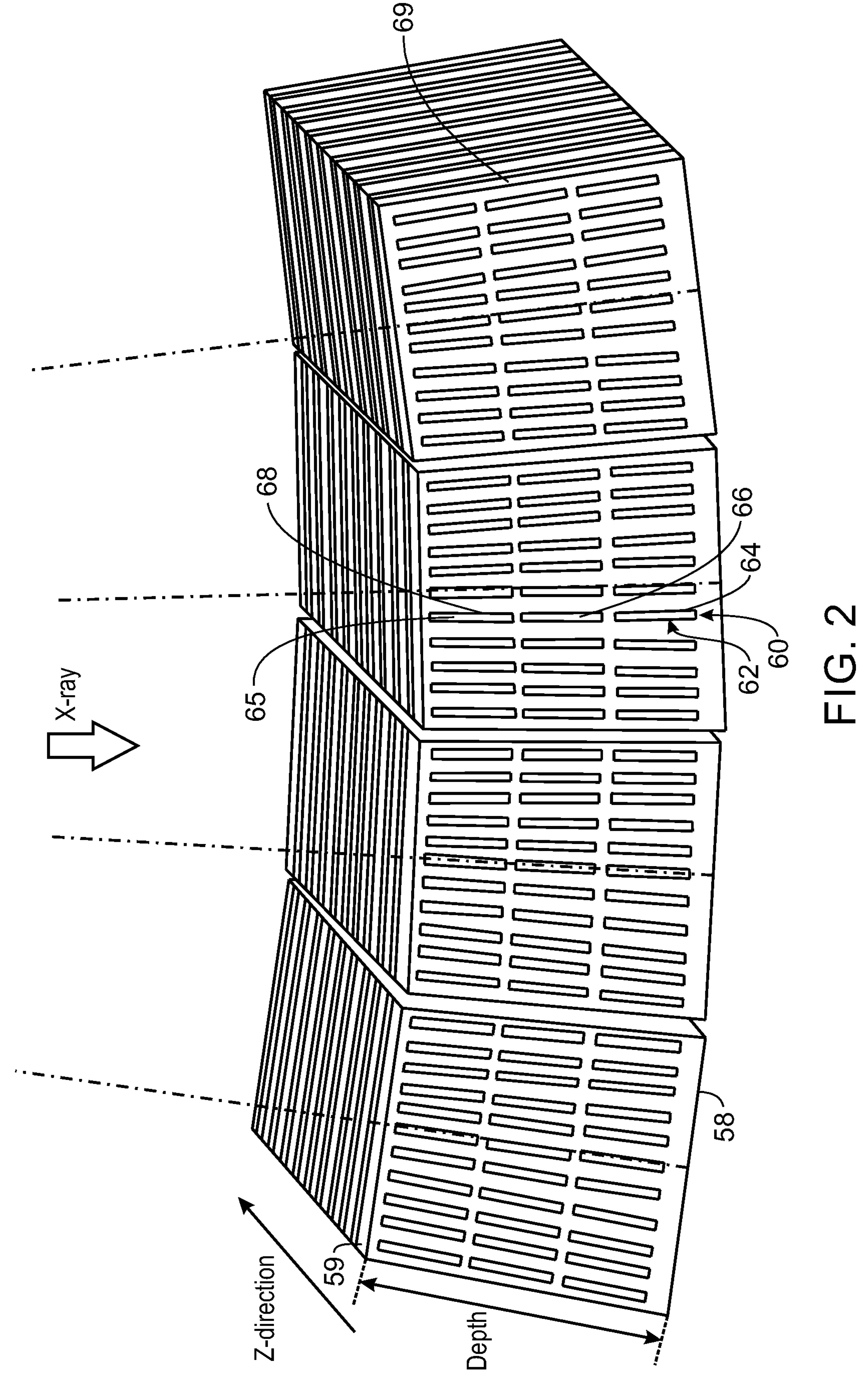
FIG. 2 is a schematic diagram illustrating an example of modular X-ray detector sub-modules arranged side-by-side and stacked one after the other, in accordance with aspects of the present disclosure.

FIG. 2 is a schematic diagram illustrating an example of a modular X-ray detector sub-module 58 (e.g., detector sensors) arranged side-by-side and stacked one after the other. The detector sub-modules 58 may be edge-on detector sub-modules. As depicted, X-rays enter through an edge 59 of the detector sub-module 58. A guard ring may extend along the edges 59 of the detector sub-module 58 to protect the detector sub-module 58 from electrical breakdown and isolate the detector area from excessive leakage current. In certain embodiments, the detector sub-modules 58 may be planar modules. The X-ray detector sub-modules 58 may be stacked one after the other to form larger detector modules that may be assembled together side-by side to build up an overall X-ray detector. The detector sub-modules 58 may generally be arranged side-by-side, e.g., in a slightly curved overall configuration, in a direction substantially perpendicular to the z-direction. In certain embodiments, the detector sub-modules 58 may be stacked one after the other in the z-direction.

As depicted, each detector sub-module 58 includes a plurality of detector elements 60 (e.g., pixels such photodiodes or diodes). The detector elements 60 may be elongated electrodes (e.g., metal photodiode electrodes) with the length extension directed towards a focal point of an X-ray system. Depending on the detector topology, the detector element 60 may correspond to a pixel. In certain embodiments, the detector sub-module 58 may be a depth-segmented detector sub-module having a number of detector strips 62 with each strip 62 having a number of depth segments 65. As depicted, each strip 62 has a first segment 64, a second segment 66, and a third segment 68 associated with a different depth (relative to the focal point) along a detection line. As depicted, at least portions of each segment 64, 66, 68 are co-linearly arranged. The number of segments 65 may vary (e.g., 1 to 3 or more). For such a depth-segmented detector sub-module 58, each depth segment 65 may be regarded as an individual detector element (if each depth segment is associated with its own individual charge collecting electrode). In certain embodiments, circuitry may treat the depth segments 65 of a single strip 62 logically as a single detector element.

The shape of the detector sub-module 58 may vary. In certain embodiments, the detector sub-module 58 may have a parallelogram shape, a trapezoidal shape, a triangular shape, or another shape. In certain embodiments, one or more edges 59 of the detector sub-module 58 may be slanted. The shapes of the detector elements 60 may vary. In certain embodiments, the detector elements 60 arranged along a slanted side edge 69 of the detector sub-module 58 may include tapered edge segments (e.g., trapezoidal or triangular segments and/or truncated trapezoidal or triangular segments with rounded corners). In certain embodiments, a segment 65 of a strip 62 that is closest to a slanted side edge of a detector sub-module 58 may be orientated so that it extends into an area of an adjacent strip 62. In certain embodiments, the segments 65 may also be slanted.

Figure 3:
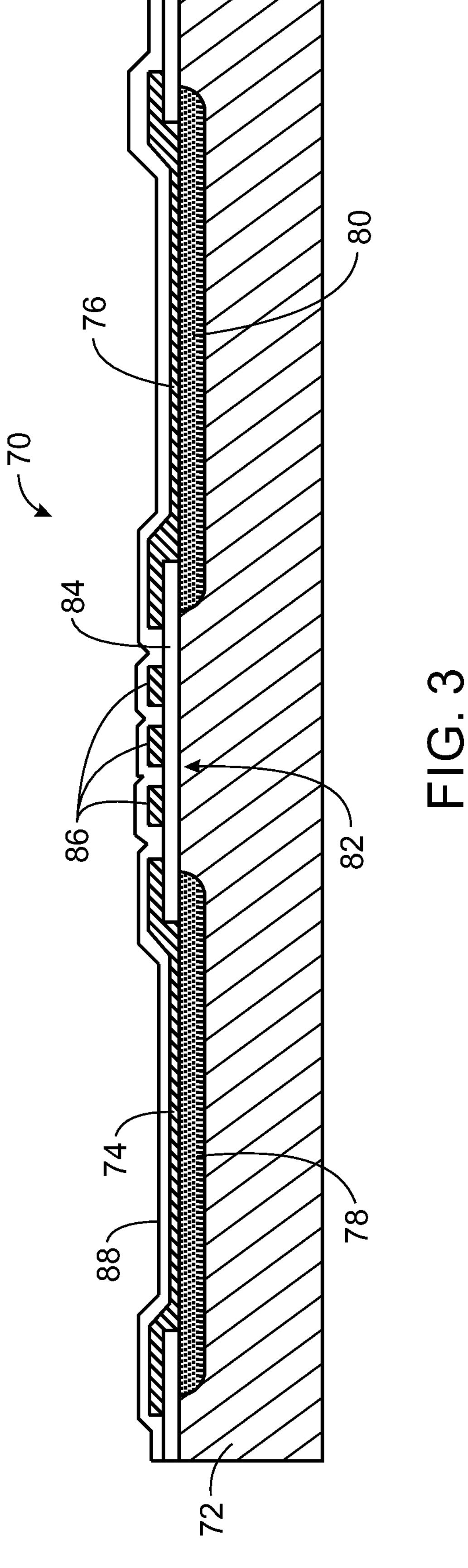
FIG. 3 is a cross-sectional view through a portion of an X-ray detector sub-module, in accordance with aspects of the present disclosure.

FIG. 3 is a cross-sectional view through a portion of the X-ray detector sub-module 70. The X-ray detector sub-module 70 includes a semiconductor layer 72. The semiconductor layer 72 is made of silicon. In certain embodiments, the semiconductor layer 72 may be made of gallium arsenide, cadmium zinc telluride, or another semiconductor material. Detector elements or segments 74, 76 (e.g., metal photodiode electrodes) are disposed on the semiconductor layer 72. The electrodes may be made of aluminum. In particular, the electrodes 74, 76 are disposed on doped implants 78, 80 (e.g., p-type or n-type silicon implants depending on whether the silicon of the semiconductor layer is n-type or p-type) that are disposed on the semiconductor layer 72. The detector elements 74, 76 may be respective segments for different strips of segments disposed adjacent to each other. The detector elements 74, 76 and the doped implants 78, 80 are disposed on the semiconductor layer 72 spaced apart so that a gap 82 is formed between them. The X-ray detector sub-module 70 includes an electrical insulator layer 84 extending between the adjacent electrodes 74, 76. The electrical insulator layer 84 may be silicon dioxide, silicon nitride, polyimide, spin-on glass, or another insulating material. One or more wiring traces 86 (e.g., metal traces) are routed within the gap 82 between the electrodes 74, 76. As depicted, the wiring traces 86 are disposed on the electrical insulator layer 84. As depicted, the wiring traces 86 are disposed in an evenly spaced manner across the gap 82. In certain embodiments, the wiring traces 86 may be routed as close as possible to the edges of the electrodes 74, 76. The wiring traces 86 may be coupled to the electrodes 74, 76 or different electrodes. The wiring traces 86 are routed along the gap 82 (and possibly other gaps) to readout circuitry. As depicted, a passivation layer 88 is disposed over these components of the X-ray detector sub-module 70. The passivation layer 88 may be made of silicon oxide, silicon nitride or another insulator.

Figure 4:
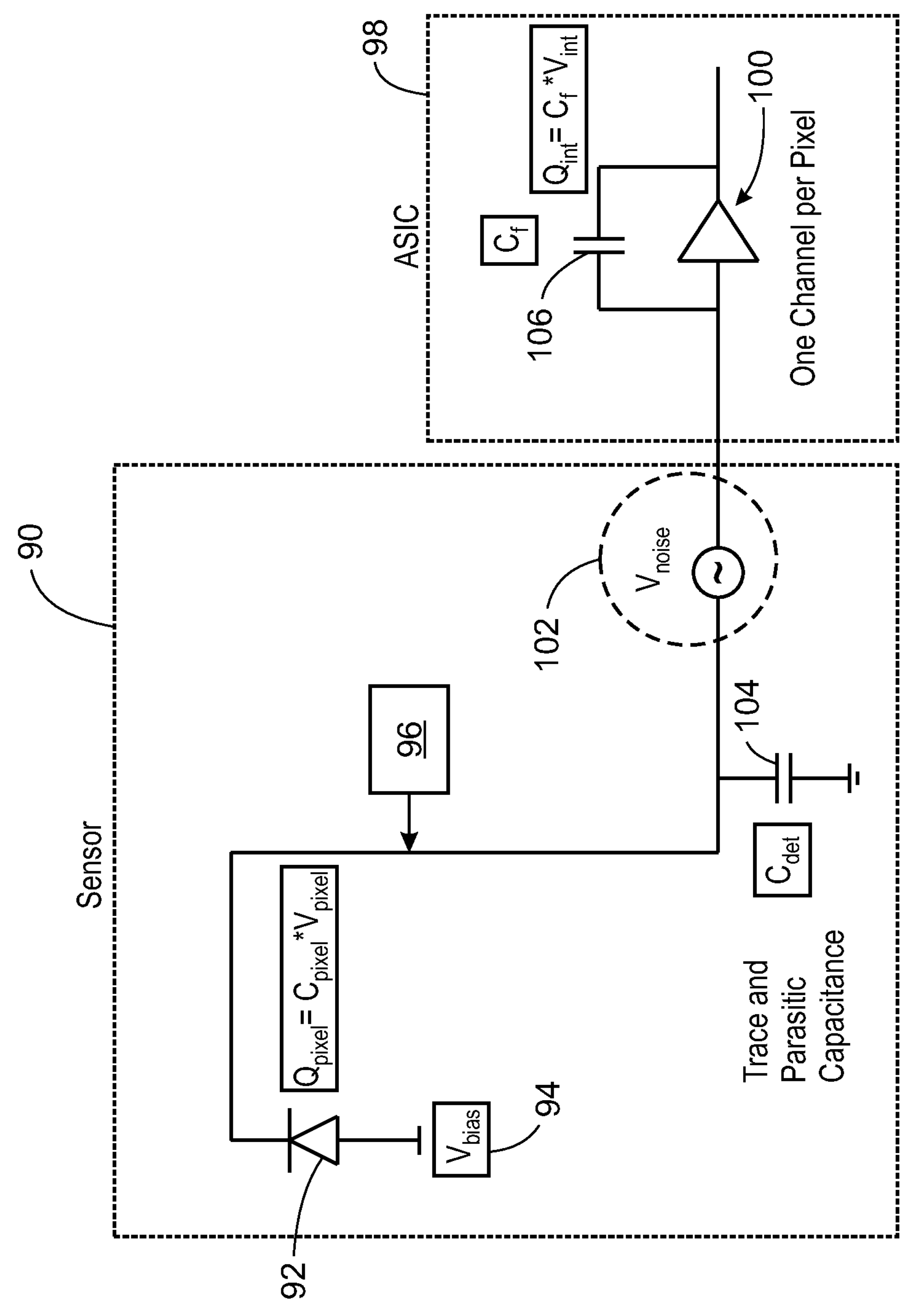
FIG. 4 is a schematic diagram illustrating a portion of a prior art X-ray detector sub-module having a passive pixel.

FIG. 4 is a schematic diagram illustrating a portion of a prior art X-ray detector sub-module 90 (detector sensor) having a passive pixel (i.e., instantly read out without pixel-based amplification). As depicted, the X-ray detector sub-module 90 includes a photodiode or diode 92 (e.g., pixel or detector element). The X-ray detector sub-module 90 may include a plurality of photodiodes 92. A voltage bias 94 is applied to the photodiode 92. The photodiode 92 is coupled to a trace 96 (e.g., conductive metal trace). The trace 96 is a data line (e.g., dedicated data line) coupled to readout circuitry 98 (e.g., front-end of ASIC) for reading the outputted signal (e.g., current pulse) from the photodiode 92 in response to detecting an incident X-ray photon (e.g., absorbed by the semiconductor layer). The readout circuitry 98 is separate from the X-ray detector sub-module 90 (i.e., not disposed on a semiconductor layer of the X-ray detector sub-module 90). Each photodiode 92 is coupled to a dedicated channel (e.g., dedicated readout channel) of the readout circuitry 98. The traces 96 of the photodiodes 92 are coupled to the readout circuitry 98 by direct wire-bonding. This heterogenous integration puts a large capacitance load to the input CSA 100 of the readout circuitry 98 (e.g., ASIC). In particular, noise 102 in the trace 96 or the readout circuitry 98 is amplified by the ratio of the detector capacitance ($C_{det}$) 104 to the feedback capacitance ($C_f$) 106 of the readout circuitry 98 (e.g., ASIC). Besides increasing the noise, the large capacitance load also increases power consumption of the system.

Figure 5:
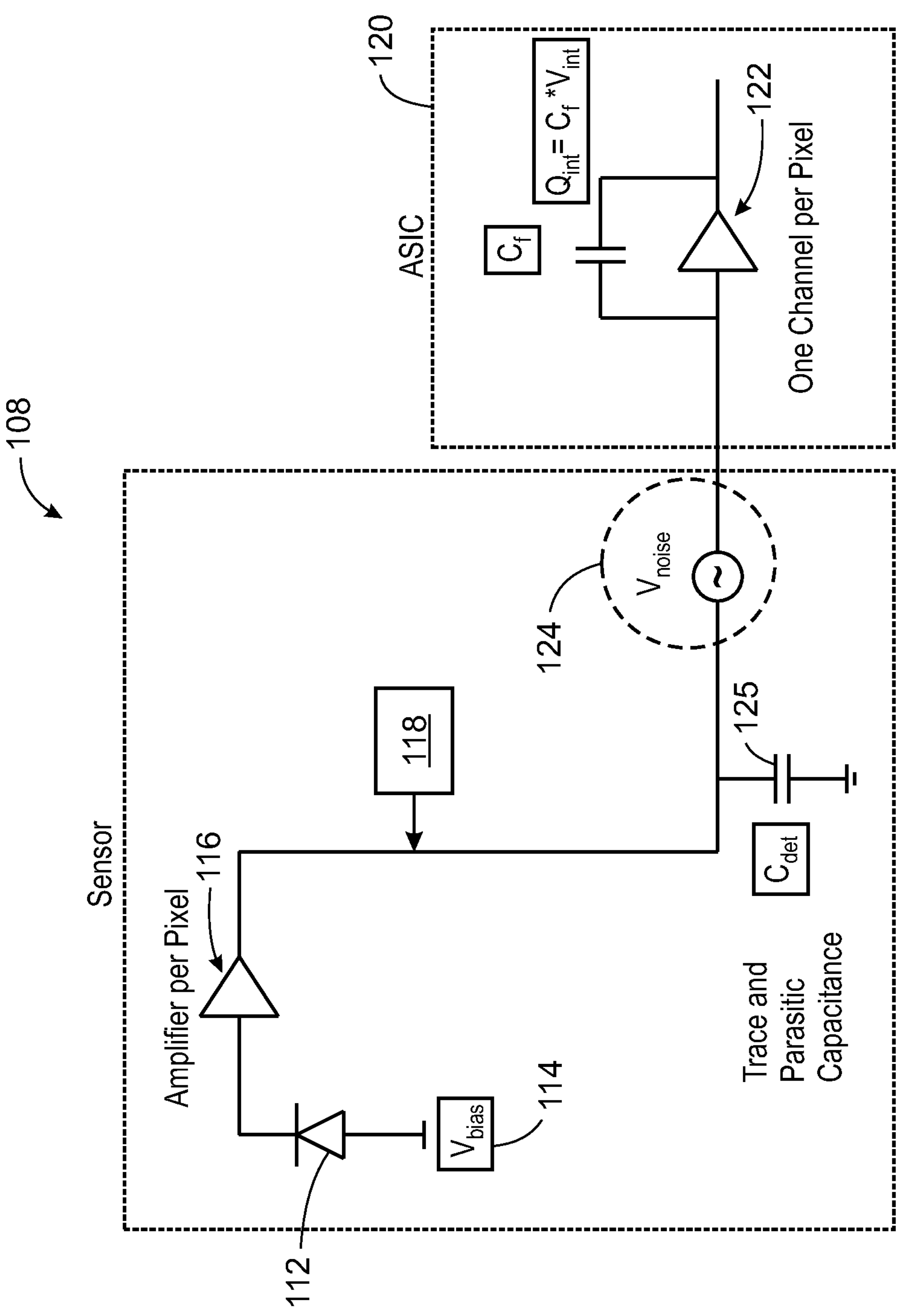
FIG. 5 is a schematic diagram illustrating a portion of an X-ray detector sub-module having an active pixel, in accordance with aspects of the present disclosure.

FIG. 5 is a schematic diagram illustrating a portion of an X-ray detector sub-module 108 (detector sensor) having an active pixel (i.e., including some form of amplification). The X-ray detector sub-module 108 is similar to the detector sub-modules 58 and 70 in FIGS. 2 and 3. As depicted, the X-ray detector sub-module 110 includes a photodiode or diode 112 (e.g., active pixel or detector element). The X-ray detector sub-module 110 may include a plurality of photodiodes 112. A voltage bias 114 is applied to the photodiode 112. The photodiode 112 is coupled to an amplification stage 116 (i.e., the amplification stage 116 is integrated with the active pixel). The amplification stage 116 is configured to generate an output signal based on a current pulse output generated by the active pixel in response to detecting an incident X-ray photon (e.g., absorbed by the semiconductor layer). The amplification stage 116 is coupled to a trace 118 (e.g., conductive metal trace). The trace 118 is a data line (e.g., dedicated data line) coupled to readout circuitry 120 (e.g., front-end of ASIC) for reading the outputted signal from the amplification stage 116. The readout circuitry 120 is separate from the X-ray detector sub-module 108 (i.e., not disposed on a semiconductor layer of the X-ray detector sub-module 108). Each photodiode 116 is coupled to a dedicated channel (e.g., dedicated readout channel) of the readout circuitry 120. The traces 118 of the photodiodes 112 are directly coupled to the readout circuitry 120 by direct wire-bonding. The photodiodes 112 do not store the detected charge and, thus, are directly coupled to the readout circuitry 120 and, in certain embodiments, provided to the input CSA 122 of the readout circuitry 120 (e.g., ASIC). Noise 124 in the trace 118 or the readout circuitry 120 is still present. However, the amplification stage 116 boosts the signal (i.e., provides current gain) from the photodiode 112 to increase the signal-to-noise ratio. In addition, the impact of the detector capacitance ($C_{det}$) 125 (i.e., trace and parasitic capacitance) on the noise 124 is suppressed.

In certain embodiments, each active pixel (e.g., photodiode 112) is configured to act as a passive integrator. When each active pixel is a passive integrator, the amplification stage 116 includes a transconductance amplifier having a single transistor. Also, when each active pixel is a passive integrator, the current source is located in the readout circuitry 120 and is biased to the single transistor. In certain embodiments, the amplification stage 116 includes a charge sensitive amplifier. When the amplification stage 116 includes a charge sensitive amplifier, the amplification stage 116 includes a first transistor and a second transistor, where the first transistor is the charge sensitive amplifier and the second transistor is configured to convert a voltage output to current. Also, when the amplification stage 116 includes a charge sensitive amplifier, a current source is integrated in each active pixel.

The image quality of the image data obtained from the photo-counting detector is improved when utilizing X-ray detector sub-module 108 (detector sensor) having active pixels as described in FIG. 5. In addition, power consumption by the readout circuitry 120 is reduced.

In certain embodiments, instead of one or more diodes, the X-ray detector sub-module 110 includes a plurality of bipolar junction transistors (e.g., vertical bipolar junction transistors) as the active pixels (see FIGS. 11-15). In these embodiments, a separate amplification stage is not needed. Instead, the bipolar junction transistor amplifies the pulse signal generated by an X-ray photon impacting the semiconductor layer of the X-ray detector sub-module 110.

Figure 6:
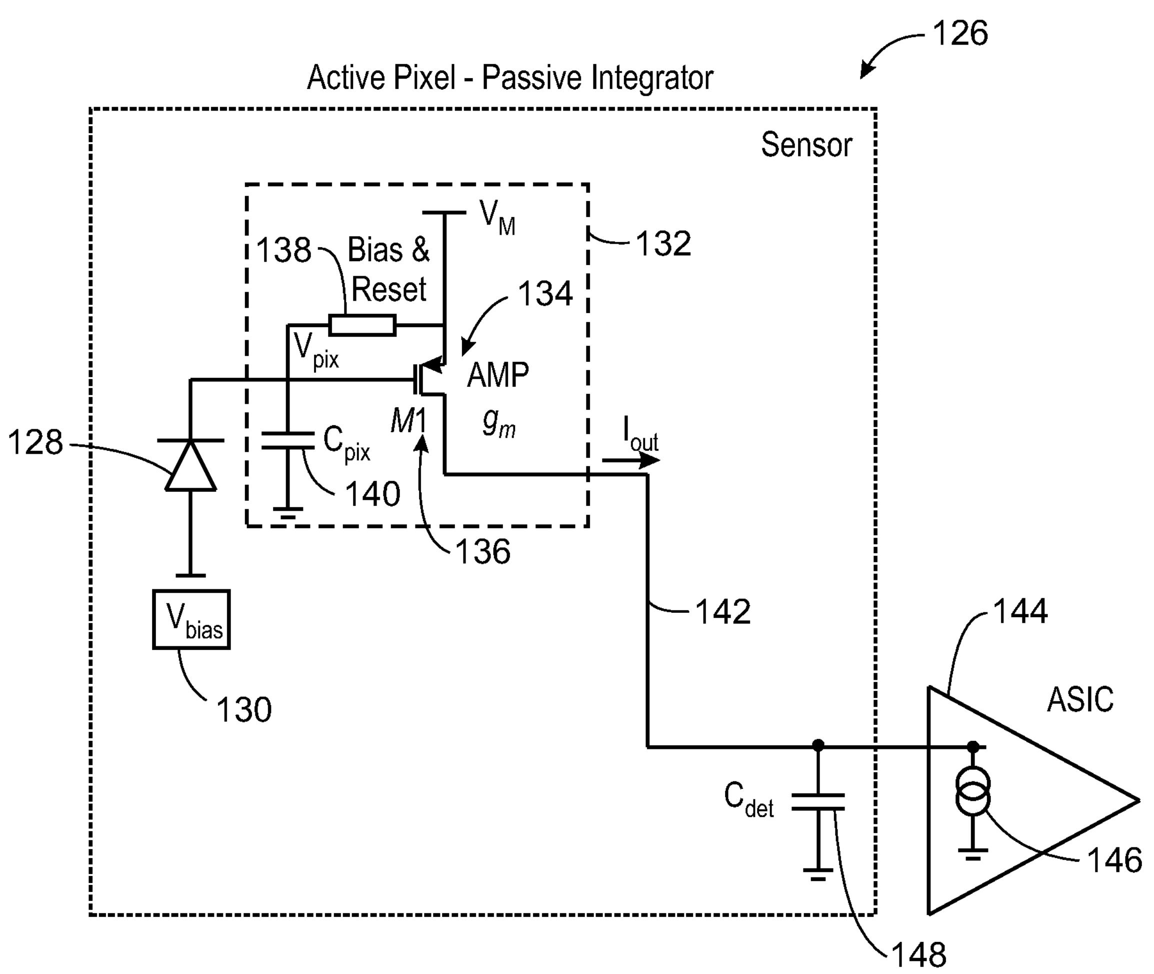
FIG. 6 is a schematic diagram illustrating a portion of an X-ray detector sub-module having an active pixel (e.g., passive integrator), in accordance with aspects of the present disclosure.

FIG. 6 is a schematic diagram illustrating a portion of an X-ray detector sub-module 126 (detector sensor) having an active pixel (e.g., passive integrator). The X-ray detector sub-module 126 is similar to the detector sub-modules 58 and 70 in FIGS. 2 and 3. As depicted, the X-ray detector sub-module 126 includes a photodiode or diode 128 (e.g., active pixel or detector element). The X-ray detector sub-module 126 may include a plurality of photodiodes 128 (see FIG. 8). A voltage bias 130 is applied to the photodiode 128. The photodiode 128 is coupled to an amplification stage 132 (i.e., the amplification stage 132 is integrated with the active pixel). The amplification stage 132 is configured to generate an output signal based on a current pulse output generated by the active pixel in response to detecting an incident X-ray photon (e.g., absorbed by the semiconductor layer).

Each active pixel (e.g., photodiode 128) is configured to act as a passive integrator. The amplification stage 132 includes a transconductance amplifier 134 (M1). In certain embodiments, the transconductance amplifier 134 is a p-channel metal-oxide semiconductor (PMOS). The transconductance amplifier 134 includes a single transistor 136. The transconductance amplifier 134 is a post-integrative amplifier that provides gain ($g_m$). The amplification stage 132 converts voltage from the photodiode 128 ($V_{pix}$) to a current ($I_{out}$). The amplification stage 132 includes a bias and reset circuit 138 coupled to the transconductance amplifier 134. The amplification stage 132 also includes a pixel capacitor 140 ($C_{pix}$). The bias and reset circuit 138 is configured to discharge the integrator (i.e. input gate capacitance). The bias and reset circuit 138 is also configured to provide a reset path for the pixel capacitor 140. The bias and reset circuit 138 ensures that only the output signal based on the current pulse output generated by the active pixel (and not bias or DC current) is provided to the feedback capacitor (see $C_f$ in the readout circuit 120 in FIG. 5).

The amplification stage 132 is coupled to a trace 142 (e.g., conductive metal trace). The trace 142 is a data line (e.g., dedicated data line) coupled to readout circuitry 144 (e.g., front-end of ASIC) for reading the outputted signal from the amplification stage 132. A current source 146 is located in the readout circuitry 144 and is biased to the single transistor 136. The readout circuitry 144 is separate from the X-ray detector sub-module 126 (i.e., not disposed on a semiconductor layer of the X-ray detector sub-module 126). Each photodiode 128 is coupled to a dedicated channel (e.g., dedicated readout channel) of the readout circuitry 144. The traces 142 of the photodiodes 128 are directly coupled to the readout circuitry 144 by direct wire-bonding. The photodiodes 128 do not store the detected charge and, thus, are directly coupled to the readout circuitry 144. The amplification stage 132 boosts the signal (i.e., provides current gain) from the photodiode 128 to increase the signal-to-noise ratio. In addition, the impact of the detector capacitance ($C_{det}$) 148 on the noise is suppressed.

The image quality of the image data obtained from the photo-counting detector is improved when utilizing X-ray detector sub-module 126 (detector sensor) having active pixels as described in FIG. 6. In addition, power consumption by the readout circuitry 144 is reduced.

Figure 7:
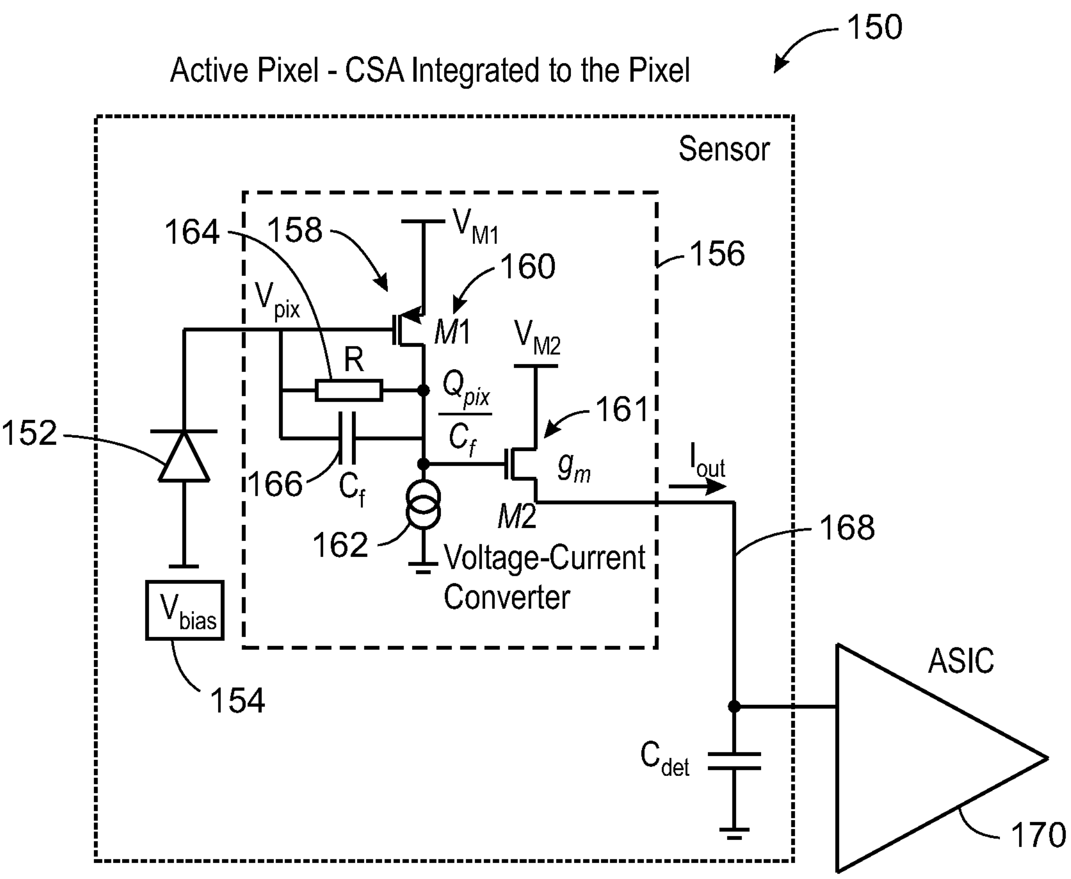
FIG. 7 is a schematic diagram illustrating a portion of an X-ray detector sub-module having an active pixel (e.g., having CSA integrated to the pixel), in accordance with aspects of the present disclosure.

FIG. 7 is a schematic diagram illustrating a portion of an X-ray detector sub-module 150 (detector sensor) having an active pixel (e.g., having CSA integrated to the pixel). The X-ray detector sub-module 150 is similar to the detector sub-modules 58 and 70 in FIGS. 2 and 3. As depicted, the X-ray detector sub-module 150 includes a photodiode or diode 152 (e.g., active pixel or detector element). The X-ray detector sub-module 126 may include a plurality of photodiodes 152 (see FIG. 9). A voltage bias 154 is applied to the photodiode 152. The photodiode 152 is coupled to an amplification stage 156 (i.e., the amplification stage 156 is integrated with the active pixel). The amplification stage 156 is configured to generate an output signal based on a current pulse output generated by the active pixel in response to detecting an incident X-ray photon (e.g., absorbed by the semiconductor layer).

Each active pixel (e.g., photodiode 152) is configured to act as a passive integrator. The amplification stage 156 includes a charge sensitive amplifier 158 (M1). The charge sensitive amplifier 158 integrated in the active pixel. The amplification stage 156 includes a first transistor 160 and a second transistor 161. In certain embodiments, both the first transistor 160 and the second transistor 161 are PMOSs. In certain embodiments, the first transistor 160 is a PMOS and the second transistor 161 is an n-channel metal-oxide semiconductor (NMOS). There is no need for biasing of the first transistor 160. If the second transistor 161 is an NMOS then it acts as a source follower (e.g., voltage buffer). As a result, the readout circuitry 170 (e.g., ASIC) needs only a shaper and discriminator. If the second transistor 161 is a PMOS then it is a two stage gain and the readout circuitry 170 needs a CSA, shaper, and discriminator. The first transistor 160 is the charge sensitive amplifier 158. The CSA amplifier 158 is a transconductance amplifier that provides gain. The second transistor 161 (M2) is configured to convert voltage from the charge sensitive amplifier 158 to a current ($I_{out}$). The second transistor 161 also provides additional gain. As depicted in FIG. 7, the amplification stage 156 includes a current source 162 integrated in each active pixel. The amplification stage 156 includes a resistor (R) 164. The amplification stage 156 also includes a feedback capacitor 166 ($C_f$).

The amplification stage 156 is coupled to a trace 168 (e.g., conductive metal trace). The trace 168 is a data line (e.g., dedicated data line) coupled to readout circuitry 170 (e.g., front-end of ASIC) for reading the outputted signal from the amplification stage 156. The readout circuitry 170 is separate from the X-ray detector sub-module 150 (i.e., not disposed on a semiconductor layer of the X-ray detector sub-module 150). Each photodiode 152 is coupled to a dedicated channel (e.g., dedicated readout channel) of the readout circuitry 170. The traces 168 of the photodiodes 152 are directly coupled to the readout circuitry 170 by direct wire-bonding. The photodiodes 152 do not store the detected charge and, thus, are directly coupled to the readout circuitry 170. The amplification stage 156 boosts the signal (i.e., provides current gain) from the photodiode 152 to increase the signal-to-noise ratio. In addition, the impact of the detector capacitance ($C_{det}$) 172 on the noise is suppressed.

The image quality of the image data obtained from the photo-counting detector is improved when utilizing X-ray detector sub-module 150 (detector sensor) having active pixels as described in FIG. 7. In addition, power consumption by the readout circuitry 170 is reduced.

Figure 8:
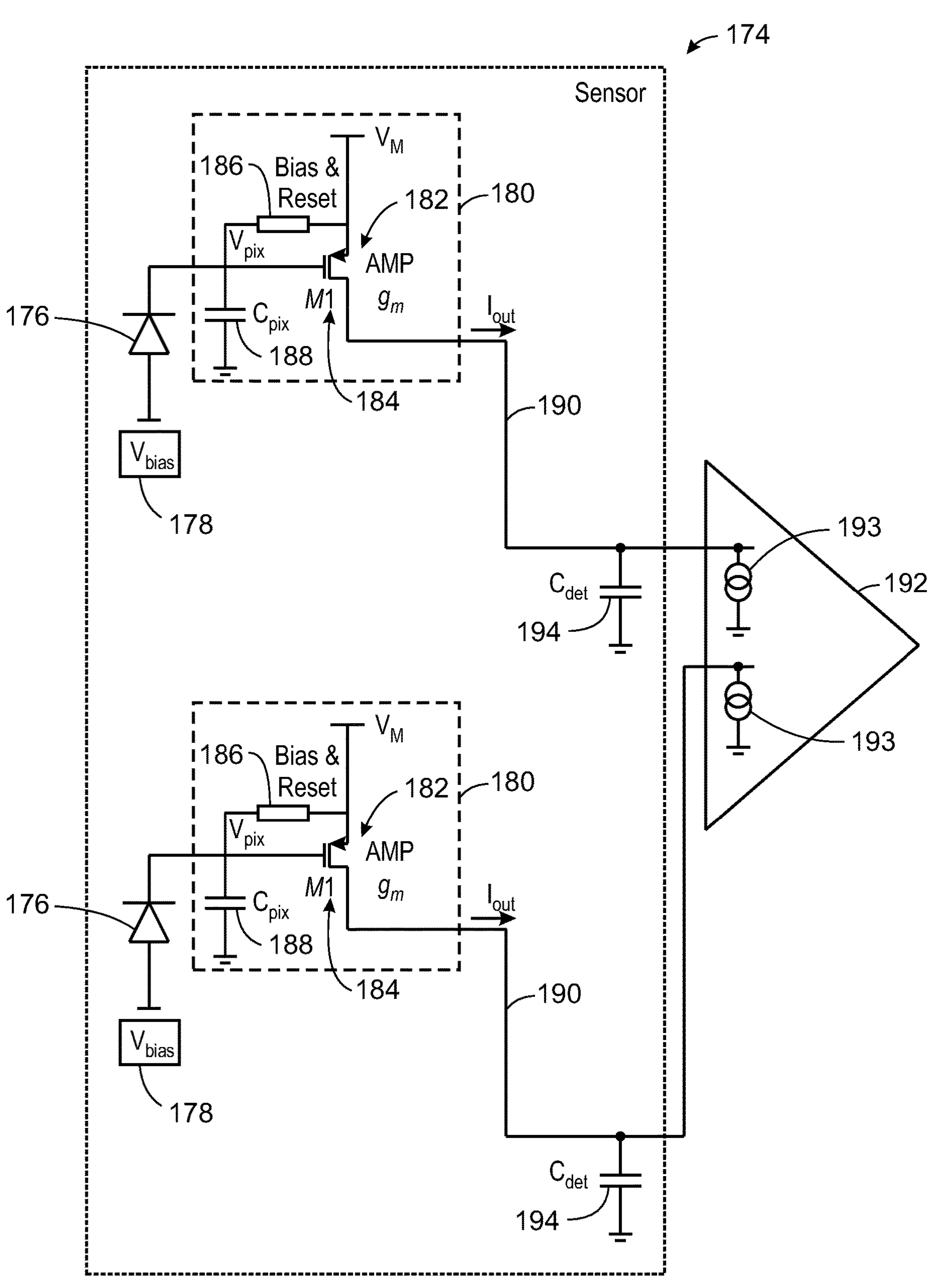
FIG. 8 is a schematic diagram illustrating a portion of an X-ray detector sub-module having a plurality of active pixels (e.g., passive integrators), in accordance with aspects of the present disclosure.

FIG. 8 is a schematic diagram illustrating a portion of an X-ray detector sub-module 174 (detector sensor) having a plurality of active pixels (e.g., passive integrators). The X-ray detector sub-module 174 is similar to the detector sub-modules 58 and 70 in FIGS. 2 and 3. As depicted, the X-ray detector sub-module 174 includes a plurality of photodiodes or diodes 176 (e.g., active pixel or detector element). A voltage bias 178 is applied to each photodiode 176. Each photodiode 176 is coupled to a respective amplification stage 180 (i.e., each amplification stage 180 is integrated with its respective active pixel). Each amplification stage 180 is configured to generate an output signal based on a current pulse output generated by a respective active pixel in response to detecting an incident X-ray photon (e.g., absorbed by the semiconductor layer).

Each active pixel (e.g., photodiode 176) is configured to act as a passive integrator. Each amplification stage 180 includes a transconductance amplifier 182 (M1). Each transconductance amplifier 182 includes a single transistor 184. Each transconductance amplifier 182 is a post-integrative amplifier that provides gain ($g_m$). In certain embodiments, each transconductance amplifier 182 is a PMOS. Each amplification stage 180 converts voltage from a respective photodiode 176 ($V_{pix}$) to a current ($I_{out}$). Each amplification stage 180 includes a bias and reset circuit 186. Each 180 amplification stage 182 includes a bias and reset circuit 186 coupled to the transconductance amplifier 182. Each amplification stage 180 also includes a pixel capacitor 188 ($C_{pix}$). Each bias and reset circuit 186 is configured to discharge the integrator (i.e. input gate capacitance). Each bias and reset circuit 186 is also configured to provide a reset path for the pixel capacitor 188. Each bias and reset circuit 186 ensures that only the output signal based on the current pulse output generated by the active pixel (and not bias or DC current) is provided to the feedback capacitor (see $C_f$ in the readout circuit 120 in FIG. 5).

Each amplification stage 180 is coupled to a respective trace 190 (e.g., conductive metal trace). Each trace 190 is a data line (e.g., dedicated data line) coupled to readout circuitry 192 (e.g., front-end of ASIC) for reading the outputted signal from the respective amplification stage 180. A respective current source 193 is located in the readout circuitry 192 and is biased to a respective transistor 184. The readout circuitry 190 is separate from the X-ray detector sub-module 174 (i.e., not disposed on a semiconductor layer of the X-ray detector sub-module 174). Each photodiode 176 is coupled to a dedicated channel (e.g., dedicated readout channel) of the readout circuitry 192. In certain embodiments, the readout channels for the plurality of photodiodes 176 are located on the same ASIC module. In certain embodiments, the readout channels for the plurality of photodiodes 176 are located on different ASIC modules. The traces 190 of the photodiodes 176 are directly coupled to the readout circuitry 192 by direct wire-bonding. The photodiodes 176 do not store the detected charge and, thus, are directly coupled to the readout circuitry 192. Each amplification stage 180 boosts the signal (i.e., provides current gain) from the respective photodiode 176 to increase the signal-to-noise ratio. In addition, the impact of the detector capacitance ($C_{det}$) 194 on the noise is suppressed.

The image quality of the image data obtained from the photo-counting detector is improved when utilizing X-ray detector sub-module 174 (detector sensor) having active pixels as described in FIG. 8. In addition, power consumption by the readout circuitry 192 is reduced.

Figure 9:
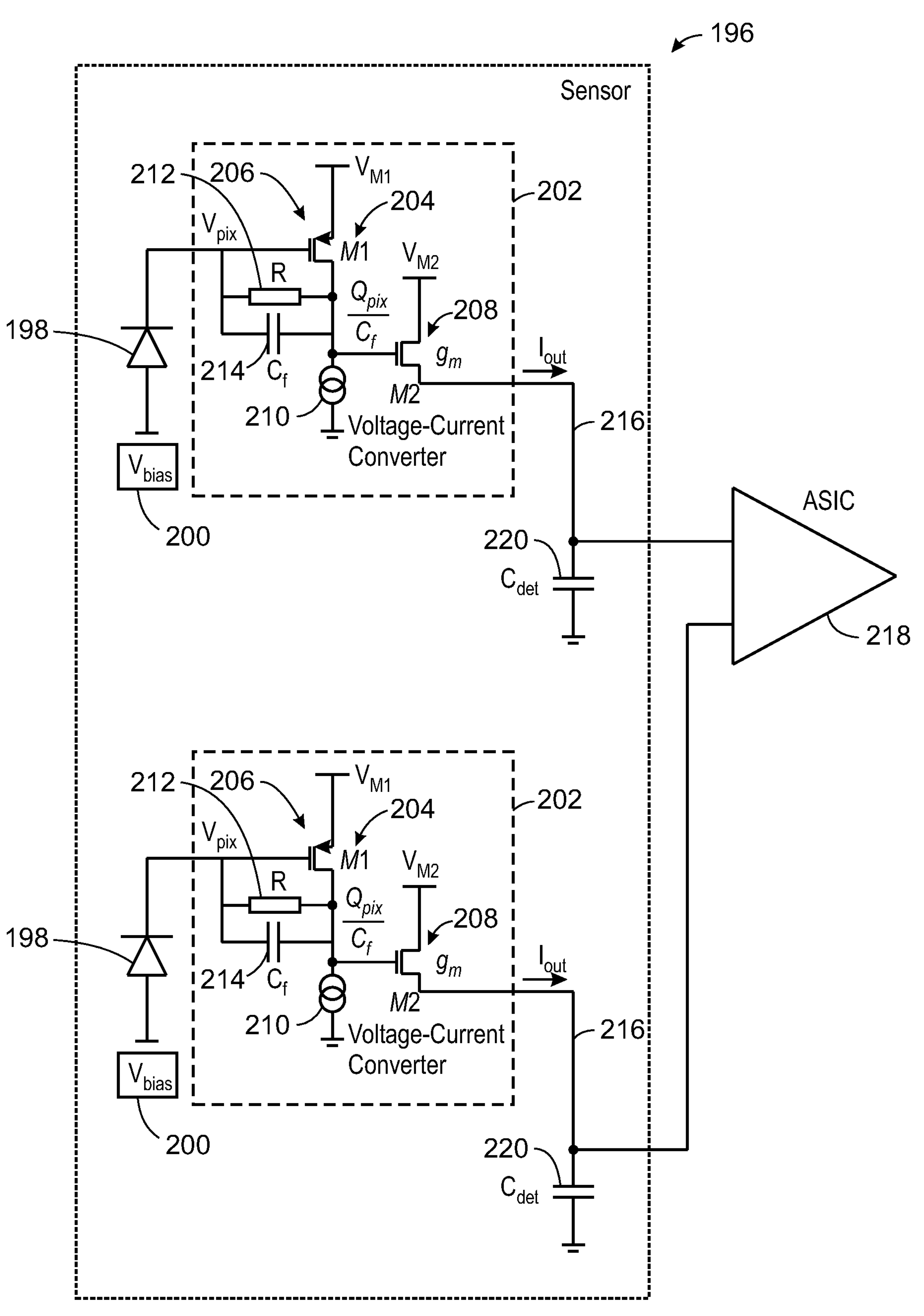
FIG. 9 is a schematic diagram illustrating a portion of an X-ray detector sub-module having a plurality of active pixels (e.g., each with CSA integrated), in accordance with aspects of the present disclosure.

FIG. 9 is a schematic diagram illustrating a portion of an X-ray detector sub-module 196 (detector sensor) having a plurality of active pixels (e.g., each with CSA integrated). The X-ray detector sub-module 196 is similar to the detector sub-modules 58 and 70 in FIGS. 2 and 3. As depicted, the X-ray detector sub-module 196 includes a plurality of photodiodes or diodes 198 (e.g., active pixel or detector element). A voltage bias 200 is applied to each photodiode 198. Each photodiode 198 is coupled to a respective amplification stage 202 (i.e., each amplification stage 202 is integrated with its respective active pixel). Each amplification stage 202 is configured to generate an output signal based on a current pulse output generated by its respective active pixel in response to detecting an incident X-ray photon (e.g., absorbed by the semiconductor layer).

Each active pixel (e.g., photodiode 198) is configured to act as a passive integrator. Each amplification stage 202 includes a respective charge sensitive amplifier 204 (M1). Each charge sensitive amplifier 204 is integrated in its active pixel. Each amplification stage 202 includes a respective first transistor 206 and a respective second transistor 208. In certain embodiments, both the first transistor 206 and the second transistor 208 are PMOSs. In certain embodiments, the first transistor 206 is a PMOS and the second transistor 208 is an NMOS. There is no need for biasing of the first transistor 206. Each first transistor 206 is the charge sensitive amplifier 204. Each CSA amplifier 204 is a transconductance amplifier that provides gain. Each second transistor 208 (M2) is configured to convert voltage from the respective charge sensitive amplifier 204 ($\sim V_{pix}$) to a current ($I_{out}$). Each second transistor 208 also provides additional gain. As depicted in FIG. 9, each amplification stage 202 includes a respective current source 210 integrated in each active pixel. Each amplification stage 202 includes a respective resistor (R) 212. Each amplification stage 202 also includes a respective feedback capacitor 214 ($C_f$).

Each amplification stage 202 is coupled to a respective trace 216 (e.g., conductive metal trace). Each respective trace 216 is a data line (e.g., dedicated data line) coupled to readout circuitry 218 (e.g., front-end of ASIC) for reading the outputted signal from a respective amplification stage 202. The readout circuitry 218 is separate from the X-ray detector sub-module 196 (i.e., not disposed on a semiconductor layer of the X-ray detector sub-module 196). Each photodiode 198 is coupled to a dedicated channel (e.g., dedicated readout channel) of the readout circuitry 218. In certain embodiments, the readout channels for the plurality of photodiodes 198 are located on the same ASIC module. In certain embodiments, the readout channels for the plurality of photodiodes 198 are located on different ASIC modules. The respective traces 216 of the photodiodes 198 are directly coupled to the readout circuitry 218 by direct wire-bonding. The photodiodes 198 do not store the detected charge and, thus, are directly coupled to the readout circuitry 218. Each amplification stage 202 boosts the signal (i.e., provides current gain) from the respective photodiode 198 to increase the signal-to-noise ratio. In addition, the impact of the detector capacitance ($C_{det}$) 220 on the noise is suppressed.

The image quality of the image data obtained from the photo-counting detector is improved when utilizing X-ray detector sub-module 196 (detector sensor) having active pixels as described in FIG. 9. In addition, power consumption by the readout circuitry 218 is reduced.

Figure 10:
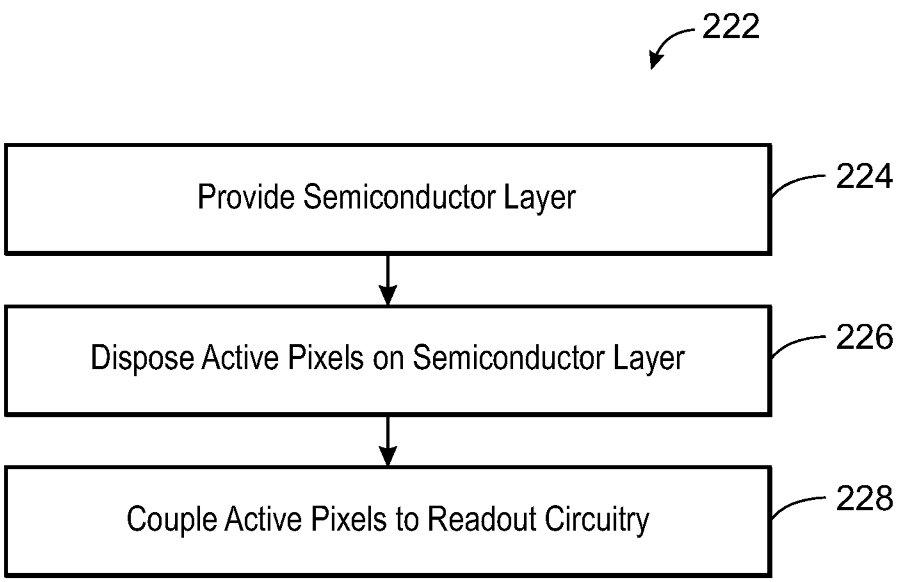
FIG. 10 is a flowchart of a method for manufacturing an X-ray detector sub-module having a plurality of pixels, in accordance with aspects of the present disclosure.

FIG. 10 is a flowchart of a method 222 for manufacturing an X-ray detector sub-module (e.g., detector sub-modules 58 and 70 in FIGS. 2 and 3) having a plurality of active pixels. The method 222 includes providing a semiconductor layer (block 224). The semiconductor layer is made of silicon. In certain embodiments, the semiconductor layer may be made of gallium arsenide, cadmium zinc telluride, or another semiconductor material.

The method 222 also includes disposing a plurality of active pixels and associated circuitry on the semiconductor layer (block 226). Each active pixel includes a photodiode coupled to an amplification stage configured to increase the gain of the signal outputted by the photodiode. In certain embodiments, each active pixel is configured to act as a passive integrator. In this embodiment, the amplification stage includes a transconductance amplifier having a single transistor. In this embodiment, the current source is located in the readout circuitry and is biased to the single transistor. In certain embodiments, the amplification stage includes a charge sensitive amplifier. In this embodiment, the amplification stage includes a first transistor and a second transistor, where the first transistor is the charge sensitive amplifier and the second transistor is configured to convert a voltage output to current. In this embodiment, a current source is integrated in each active pixel.

The method 222 further includes coupling each of the active pixels to readout circuitry (block 228). The readout circuitry may include one or more ASIC modules. Each amplification stage of each active pixel is coupled to a respective trace which serves as a data line (e.g., dedicated data line) coupled to readout circuitry (e.g., front-end of ASIC) for reading the outputted signal from the respective amplification stage. The readout circuitry is separate from the X-ray detector sub-module (i.e., not disposed on a semiconductor layer of the X-ray detector sub-module). Each photodiode (i.e., via the trace coupled to the amplification stage) is coupled to a dedicated channel (e.g., dedicated readout channel) of the readout circuitry (e.g., ASIC). In certain embodiments, the readout channels for the plurality of photodiodes are located on the same ASIC module. In certain embodiments, the readout channels for the plurality of photodiodes are located on different ASIC modules. The respective traces of the photodiodes are directly coupled to the readout circuitry by direct wire-bonding.

Figure 11:
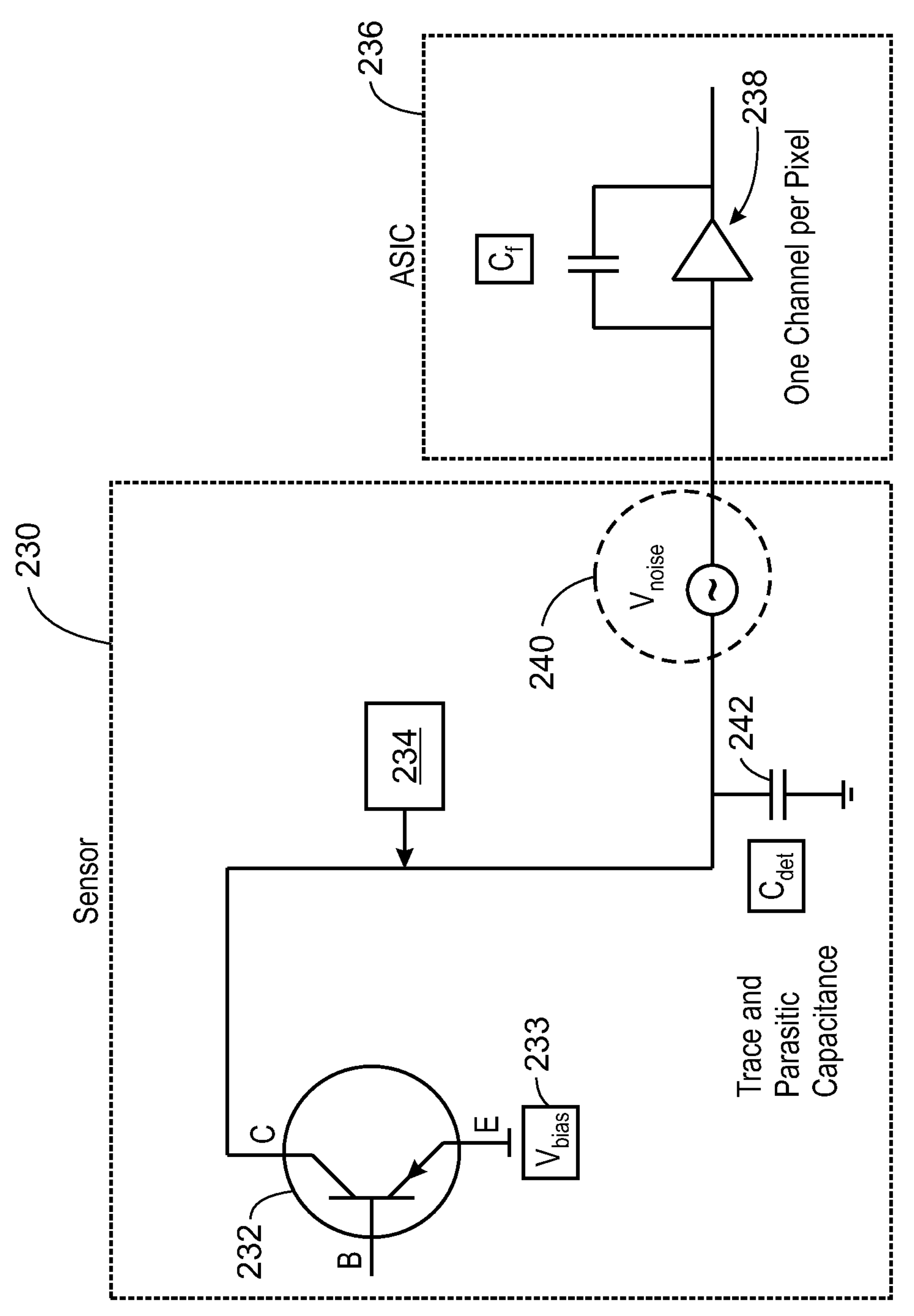
FIG. 11 is a schematic diagram illustrating a portion of an X-ray detector sub-module having an active pixel (e.g., having a bipolar junction transistor of a PNP type), in accordance with aspects of the present disclosure.
Figure 12:
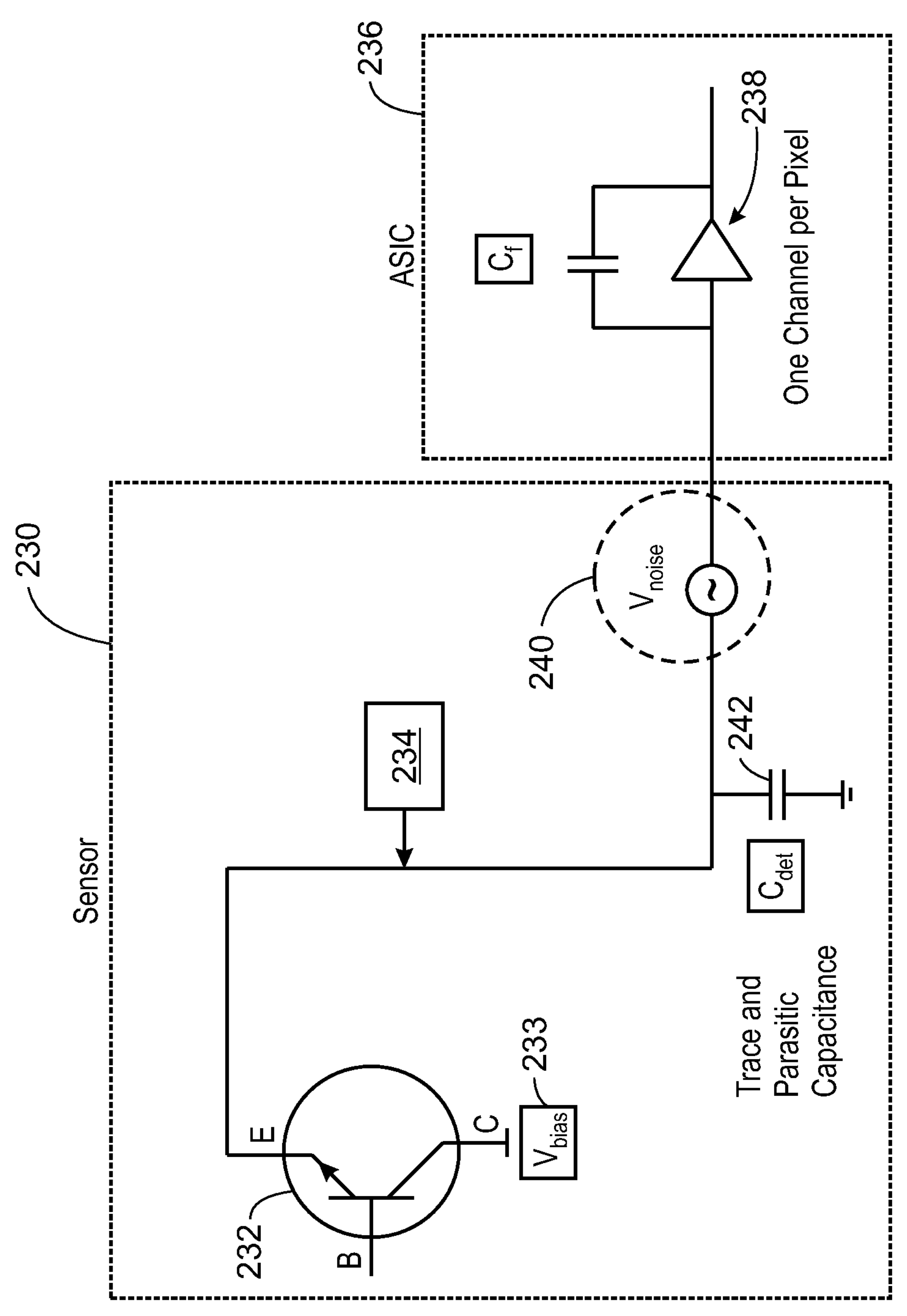
FIG. 12 is a schematic diagram illustrating a portion of an X-ray detector sub-module having an active pixel (e.g., having a bipolar junction transistor of an NPN type), in accordance with aspects of the present disclosure.

FIG. 11 is a schematic diagram illustrating a portion of an X-ray detector sub-module 230 (e.g., detector sensor) having an active pixel (e.g., having a bipolar junction transistor for amplification). The X-ray detector sub-module 230 is similar to the detector sub-modules 58 and 70 in FIGS. 2 and 3. As depicted, the X-ray detector sub-module 230 includes a bipolar junction transistor 232 (e.g., active pixel or detector element). In certain embodiments (e.g., as depicted in FIG. 12 which corresponds to the bipolar junction transistors 246 and 272 in FIGS. 13 and 14), the bipolar junction transistor 232 (e.g. vertical bipolar junction transistor) is an NPN type bipolar junction transistor. In certain embodiments (e.g., as depicted in FIG. 11 which correspond to the bipolar junction transistor 294 in FIG. 15), the bipolar junction transistor 232 is a PNP type bipolar junction transistor. The X-ray detector sub-module 230 may include a plurality of bipolar junction transistors 232. Instead of having a separate amplification stage, the bipolar junction transistor 232 provides the amplification. The bipolar junction transistor 232 is configured to generate an output signal, wherein the output signal is an amplified signal of a current pulse generated by the active pixel in response to detecting an incident X-ray photon (e.g., absorbed by the semiconductor layer). A voltage bias 233 is applied to the bipolar junction transistor 232. The bipolar junction transistor 232 is coupled to a trace 234 (e.g., conductive metal trace). The trace 234 is a data line (e.g., dedicated data line) coupled to readout circuitry 236 (e.g., front-end of ASIC) for reading the outputted signal from the bipolar junction transistor 232. The readout circuitry 236 is separate from the X-ray detector sub-module 230 (i.e., not disposed on a semiconductor layer of the X-ray detector sub-module 230). Each bipolar junction transistor 230 is coupled to a dedicated channel (e.g., dedicated readout channel) of the readout circuitry 236. The traces 234 of the bipolar junction transistors 232 are directly coupled to the readout circuitry 236 by direct wire-bonding. The bipolar junction transistors 232 do not store the detected charge and, thus, are directly coupled to the readout circuitry 236 and, in certain embodiments, provided to the input CSA 238 of the readout circuitry 236 (e.g., ASIC). Noise 240 in the trace 234 or the readout circuitry 236 is still present. However, the bipolar junction transistor 232 boosts the signal (i.e., provides current gain) to increase the signal-to-noise ratio. In addition, the impact of the detector capacitance ($C_{det}$) 242 (i.e., trace and parasitic capacitance) on the noise 240 is suppressed.

Figure 13:
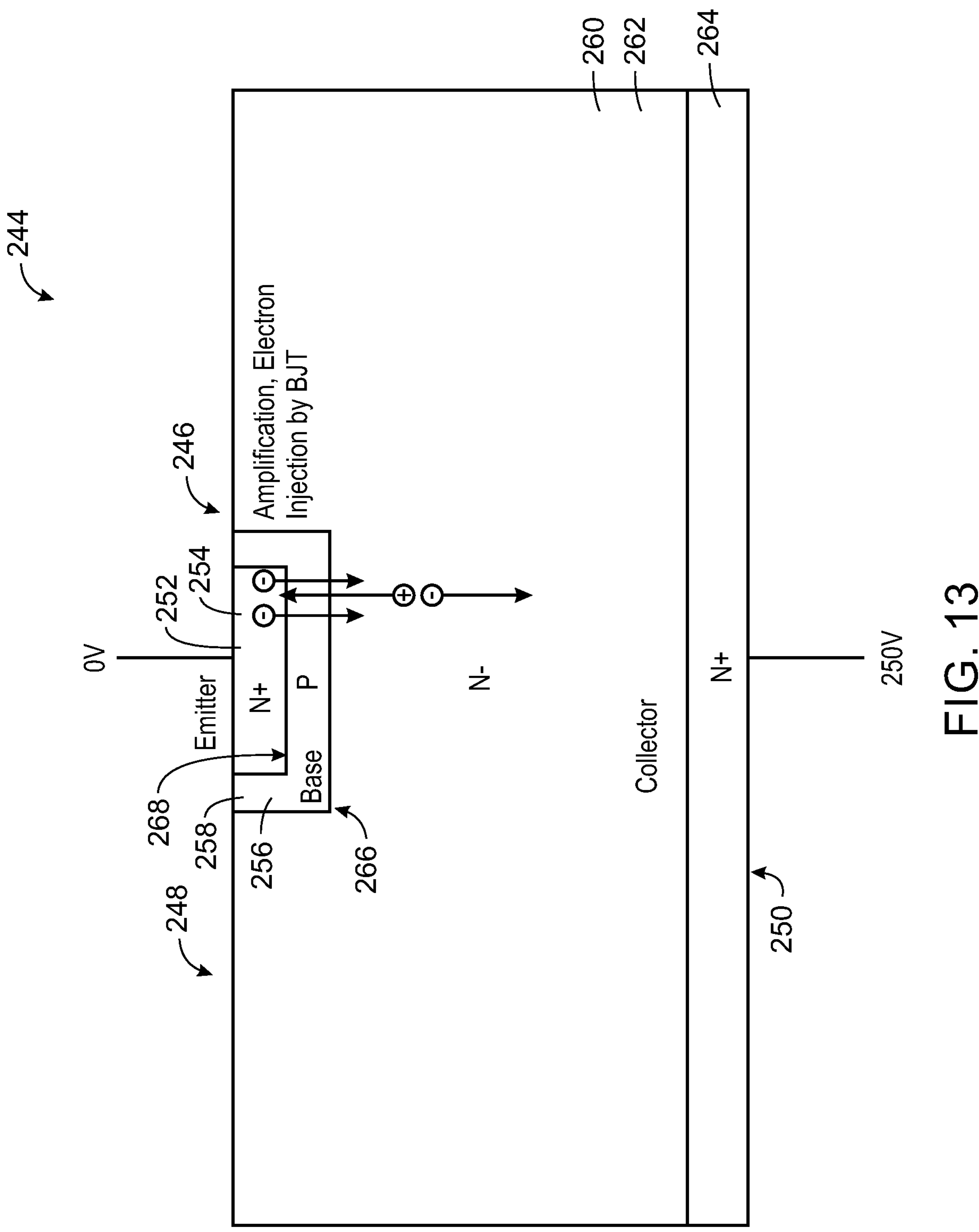
FIG. 13 is a cross-sectional view through a portion of an X-ray detector sub-module having a bipolar junction transistor (e.g., of an NPN type) illustrating its operation, in accordance with aspects of the present disclosure.

FIG. 13 is a cross-sectional view through a portion of an X-ray detector sub-module 244 having a bipolar junction transistor 246 (e.g., vertical bipolar junction transistor of an NPN type) illustrating its operation. The X-ray detector sub-module 244 includes a first side 248 (e.g. front side) and a second side 250 (back side) opposite the first side 248. As depicted, the bipolar junction transistor 246 includes an emitter 252 made of a first N-type semiconductor layer 254 (e.g., N+), a base 256 made of a P-type semiconductor layer 258 (e.g., P), and a collector 260 made of a second N-type semiconductor layer 262 (N−). The bipolar junction transistor 246 also includes a third N-type semiconductor layer 264 (e.g., N+). The collector 260 is disposed between the base 256 and the third N-type semiconductor layer 264. Both the emitter 252 and a portion of the base 256 are located on the first side 248 and the third N-type semiconductor layer 264 is located on the second side 250. The third N-type semiconductor layer 264 is more highly doped than the collector 260. The base 256 is doped 10 to 100 times lower than the emitter 252 corresponding approximately to a gain of the bipolar junction transistor 246. The P-type region of the base 256 is highly enough doped and thick enough but not too highly doped or too thick. In particular, the doping and the thickness of the base 256 is enough to avoid punch through.

A junction 266 between the base 256 and the collector 260 is reverse biased to enable full depletion. The emitter 252 is grounded. The bipolar junction transistor 246 acts as the detector element or active pixel. Electron-holes pairs (i.e., a current pulse) are generated in response to an X-ray photon travelling through the X-ray detector sub-module 244 scattering valence elections into the conduction band over an area. The holes get injected to the base 256. A buildup of excess holes forward biases a junction 268 between the emitter 252 and the base 256. Amplified electron injection to the base 256 occurs. In certain embodiments, the base 256 may need biasing. As a result, the bipolar junction transistor 246 generates an output signal, wherein the output signal is an amplified signal of a current pulse generated by the active pixel in response to an X-ray photon travelling through the semiconductor substrate.

Figure 14:
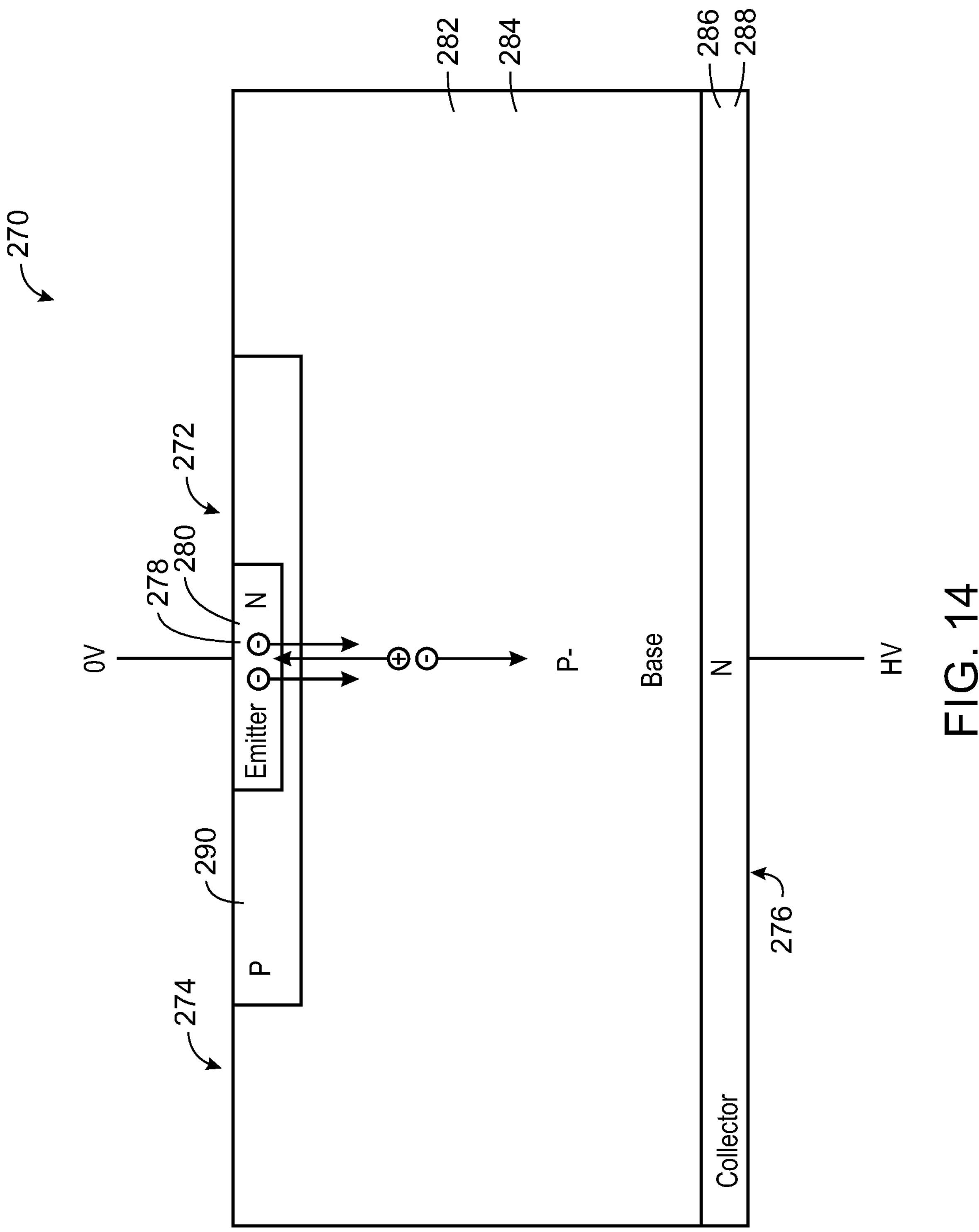
FIG. 14 is a schematic diagram illustrating a portion of an X-ray detector sub-module having a bipolar junction transistor (e.g., having an NPN type), in accordance with aspects of the present disclosure.

FIG. 14 is a schematic diagram illustrating a portion of an X-ray detector sub-module 270 having a bipolar junction transistor 272 (e.g., having an NPN type). The X-ray detector sub-module 270 includes a first side 274 (front side) and a second side 276 (back side) opposite the first side 274. As depicted, the bipolar junction transistor 272 includes an emitter 278 made of a first N-type semiconductor layer 280 (e.g., N), a base 282 made of a P-type semiconductor layer 284 (e.g., P−), and a collector 286 made of a second N-type semiconductor layer 288 (N). The bipolar junction transistor 246 also includes a second P-type semiconductor layer 290 (e.g., P). The second P-type semiconductor layer 290 is disposed between the base 282 and the emitter 278. The second P-type semiconductor layer 290 is more highly doped than the base 282. Both the emitter 278 and a portion of the second P-type semiconductor layer 290 are located on the first side 274 and the collector 286 is located on the second side 276. The P-type region is highly enough doped and thick enough but not too highly doped or too thick. Similar to as described in FIG. 13, the bipolar junction transistor 272 generates an output signal, wherein the output signal is an amplified signal of a current pulse generated by the active pixel in response to an X-ray photon travelling through the semiconductor substrate.

Figure 15:
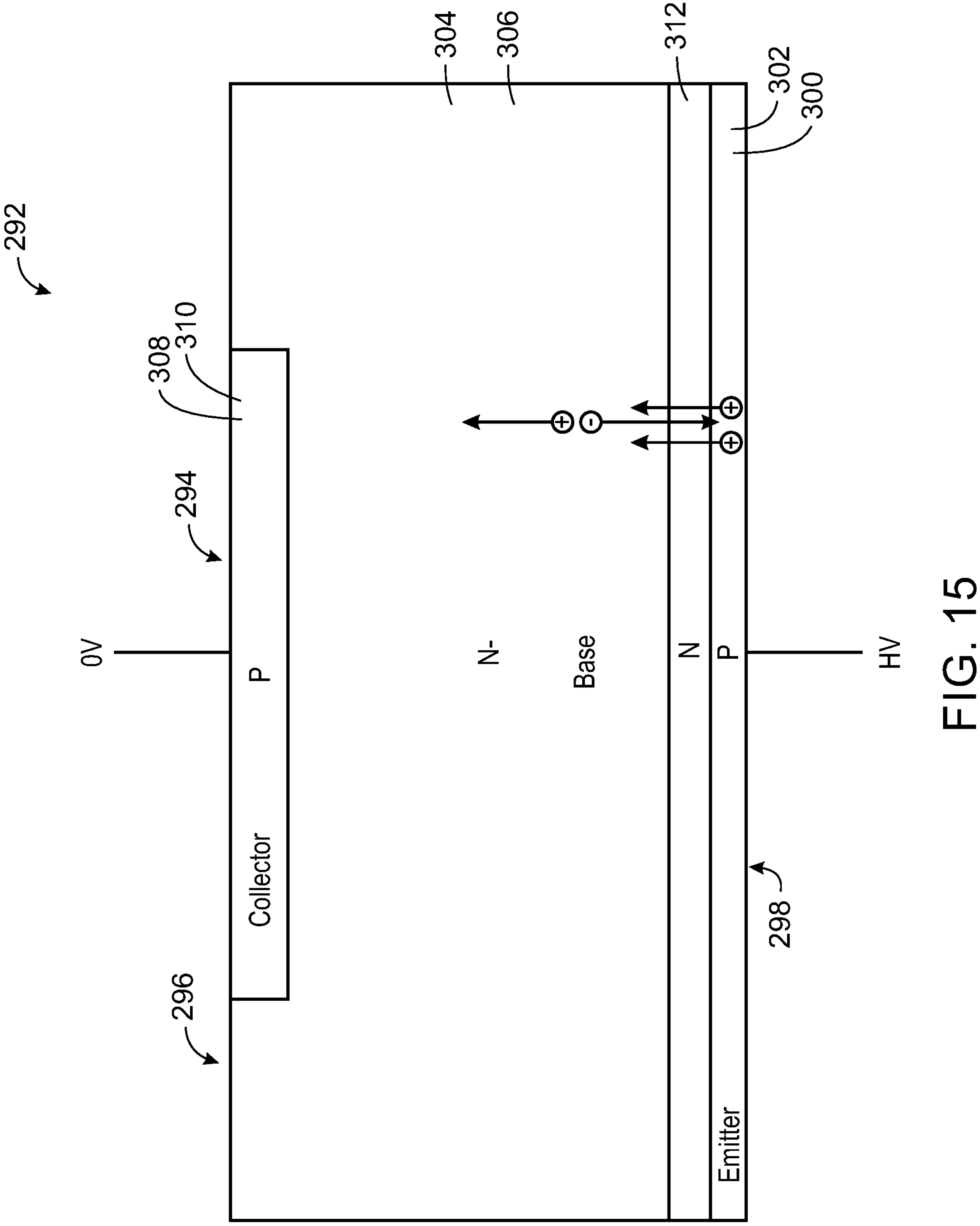
FIG. 15 is a schematic diagram illustrating a portion of an X-ray detector sub-module having a bipolar junction transistor (e.g., having a PNP type), in accordance with aspects of the present disclosure.

FIG. 15 is a schematic diagram illustrating a portion of an X-ray detector sub-module 292 having a bipolar junction transistor 294 (e.g., having a PNP type). The X-ray detector sub-module 292 includes a first side 296 (e.g., front side) and a second side 298 (e.g., back side) opposite the first side 296. As depicted, the bipolar junction transistor 272 includes an emitter 300 made of a first P-type semiconductor layer 302 (e.g., P), a base 304 made of an N-type semiconductor layer 306 (e.g., N−), and a collector 308 of a second P-type semiconductor layer 310 (e.g. P). The bipolar junction transistor 294 also includes a second N-type semiconductor layer 312 (e.g., N) disposed between the base 304 and the emitter 300. The second N-type semiconductor layer 312 is more highly doped than the base 304 to avoid punch through. The collector 308 is located on the first side 296 and the emitter 300 is located on the second side 298. The collector 308 is grounded. The bipolar junction transistor 294 acts as the detector element or active pixel. Electron-holes pairs (i.e., a current pulse) are generated in response to an X-ray photon travelling through the X-ray detector sub-module 292 scattering valence elections into the conduction band over an area. Amplified hole injection to the base 304 occurs (e.g., adjacent the second side or back side). The bipolar junction transistor 294 generates an output signal, wherein the output signal is an amplified signal of a current pulse generated by the active pixel in response to an X-ray photon travelling through the semiconductor substrate.

Technical effects of the disclosed subject matter include providing systems and methods that implement practical active pixel sensors for a photon counting system to avoid providing a large capacitance load to the input CSA of the ASIC that increases the noise and power consumption of the system. Technical effects also include improving the performance of silicon-based photon counting detectors, such as computed tomography detectors or other suitable types of radiographic X-ray detectors. Technical effects further include improving image quality due to lowering the effects of electronic noise (due to improved signal-to-noise ratio). Technical effects still further include reducing both system complexity and cost due to lower readout circuitry (e.g., ASIC) power consumption.

The techniques presented and claimed herein are referenced and applied to material objects and concrete examples of a practical nature that demonstrably improve the present technical field and, as such, are not abstract, intangible or purely theoretical. Further, if any claims appended to the end of this specification contain one or more elements designated as "means for [perform]ing [a function] . . . " or "step for [perform]ing [a function] . . . ", it is intended that such elements are to be interpreted under 35 U.S.C. 112 (f). However, for any claims containing elements designated in any other manner, it is intended that such elements are not to be interpreted under 35 U.S.C. 112 (f).

This written description uses examples to disclose the present subject matter, including the best mode, and also to enable any person skilled in the art to practice the subject matter, including making and using any devices or systems and performing any incorporated methods. The patentable scope of the subject matter is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A photon counting detector, comprising:
- a plurality of detector sub-modules, wherein each detector sub-module of the plurality of detector sub-modules comprises:
  - a semiconductor substrate; and
  - a plurality of active pixels configured to act as detector elements disposed on the semiconductor substrate; and
  - a plurality of traces extending from the plurality of active pixels to readout circuitry, wherein each active pixel of the plurality of active pixels is coupled to a respective trace of the plurality of traces, and each active pixel comprises an amplification stage configured to generate an output signal based on a current pulse output generated by the active pixel; and
- the readout circuitry configured to directly read out the output signals from the plurality of active pixels, wherein the readout circuitry is separate from the plurality of detector sub-modules in that the readout circuitry is not located on the semiconductor substrate.

2. The photon counting detector of claim 1, wherein the amplification stage is configured to generate the output signal having a higher gain than the current pulse output to increase a signal-to-noise ratio.

3. The photon counting detector of claim 1, wherein each active pixel is configured to act as a passive integrator.

4. The photon counting detector of claim 3, wherein the amplification stage of each active pixel comprises a transconductance amplifier.

5. The photon counting detector of claim 4, wherein the amplification stage of each active pixel comprises a single transistor.

6. The photon counting detector of claim 5, wherein each active pixel comprises a pixel capacitor and a bias and reset circuit, wherein the bias and reset circuit is configured to provide a reset path for the pixel capacitor and to keep bias from being provided to the readout circuitry.

7. The photon counting detector of claim 1, wherein the amplification stage of each active pixel comprises a charge sensitive amplifier.

8. The photon counting detector of claim 7, wherein the amplification stage of each active pixel comprises a first transistor and a second transistor, wherein the first transistor is the charge sensitive amplifier and the second transistor is configured to convert a voltage output to current.

9. The photon counting detector of claim 8, wherein each active pixel comprises a current source.

10. A computed tomography (CT) imaging system, comprising:
- a photon counting detector, comprising:
  - at least one detector sub-module, wherein the at least one detector sub-module comprises:
    - a semiconductor substrate; and
    - a plurality of active pixels configured to act as detector elements disposed on the semiconductor substrate; and
    - a plurality of traces extending from the plurality of active pixels to readout circuitry, wherein each active pixel of the plurality of active pixels is coupled to a respective trace of the plurality of traces, and each active pixel comprises an amplification stage configured to generate an output signal based on a current pulse output generated by the active pixel; and
  - the readout circuitry configured to directly read out the output signals from the plurality of active pixels, wherein the readout circuitry is separate from the at least one detector sub-module in that the readout circuitry is not located on the semiconductor substrate.

11. The CT imaging system of claim 10, wherein each active pixel is configured to act as a passive integrator.

12. The CT imaging system of claim 11, wherein the amplification stage of each active pixel comprises a transconductance amplifier.

13. The CT imaging system of claim 12, wherein the amplification stage of each active pixel comprises a single transistor.

14. The CT imaging system of claim 13, wherein each active pixel comprises a pixel capacitor and a bias and reset circuit, wherein the bias and reset circuit is configured to provide a reset path for the pixel capacitor and to keep bias from being provided to the readout circuitry.

15. The CT imaging system of claim 13, comprising a current source located in the readout circuitry, wherein the current source is biased to the single transistor.

16. The CT imaging system of claim 10, wherein the amplification stage of each active pixel comprises a charge sensitive amplifier, and the amplification stage of each active pixel comprises a first transistor and a second transistor, wherein the first transistor is the charge sensitive amplifier and the second transistor is configured to convert a voltage output to current.

17. The CT imaging system of claim 16, wherein each active pixel comprises a current source.

18. A photon counting detector, comprising:
- at least one detector sub-module, wherein the at least one detector sub-module comprises:
  - a semiconductor substrate; and
  - a plurality of active pixels configured to act as detector elements disposed on the semiconductor substrate; and
  - a plurality of traces extending from the plurality of active pixels to readout circuitry, wherein each active pixel of the plurality of active pixels is coupled to a respective trace of the plurality of traces, wherein each active pixel is configured to act as a passive integrator, and wherein each active pixel comprises a transconductance amplifier comprising a single transistor configured to generate an output signal based on a current pulse output generated by the active pixel; and
- the readout circuitry configured to directly read out the output signals from the plurality of active pixels, wherein the readout circuitry is separate from the at least one detector sub-module in that the readout circuitry is not located on the semiconductor substrate, and wherein the readout circuitry comprises a current source biased to the single transistor.

* * * * *